US011234689B2

(12) United States Patent
Megaro et al.

(10) Patent No.: US 11,234,689 B2
(45) Date of Patent: Feb. 1, 2022

(54) LENGTH OF SELF-RETAINING SUTURE AND METHOD AND DEVICE FOR USING THE SAME

(71) Applicant: Ethicon Inc., Somerville, NJ (US)

(72) Inventors: Anthony R. Megaro, Chapel Hill, NC (US); Matthew A. Megaro, Littleton, NC (US)

(73) Assignee: Ethicon, Inc., Somerville, NJ (US)

( * ) Notice: Subject to any disclaimer, the term of this patent is extended or adjusted under 35 U.S.C. 154(b) by 284 days.

(21) Appl. No.: 16/591,730

(22) Filed: Oct. 3, 2019

(65) Prior Publication Data

US 2020/0060675 A1 Feb. 27, 2020

Related U.S. Application Data

(63) Continuation of application No. 14/570,066, filed on Dec. 15, 2014, now Pat. No. 10,441,270, which is a
(Continued)

(51) Int. Cl.
*A61B 17/04* (2006.01)
*A61B 17/06* (2006.01)
(Continued)

(52) U.S. Cl.
CPC .... *A61B 17/0469* (2013.01); *A61B 17/06066* (2013.01); *A61B 17/06109* (2013.01);
(Continued)

(58) Field of Classification Search
CPC . A61B 17/06; A61B 17/0469; A61B 17/0483; A61B 17/06109;
(Continued)

(56) References Cited

U.S. PATENT DOCUMENTS 709,392 A 9/1902 Brown
733,723 A 7/1903 Lukens
(Continued)

FOREIGN PATENT DOCUMENTS

BE 1014364 9/2003
CA 2309844 12/1996
(Continued)

OTHER PUBLICATIONS

European Communication dated Oct. 28, 2020 for Application No. 18187211.0, 5 pages.
(Continued)

*Primary Examiner* — Tuan V Nguyen
(74) *Attorney, Agent, or Firm* — Frost Brown Todd LLC

(57) ABSTRACT

A method and device for anchoring a length of self-retaining suture. The method of anchoring includes providing for an assembly having a length of self-retaining suture and a suture insertion device. The length of suture includes at least a portion of the length having a plurality of retainers thereon extending in a first direction. The insertion device has a length and a recess to receive a portion of the suture length. The method further includes placing a portion of the suture length in the recess and inserting the device into the body of a mammal until the recess reaches a predetermined location thereby forming an insertion pathway. The method further includes retrieving the insertion device from the body by moving the insertion device in a direction substantially opposed to the insertion pathway.

20 Claims, 8 Drawing Sheets

Related U.S. Application Data continuation of application No. 13/127,220, filed as application No. PCT/US2009/063081 on Nov. 3, 2009, now Pat. No. 8,932,328.

(60) Provisional application No. 61/110,952, filed on Nov. 3, 2008.

(51) Int. Cl.
 *A61F 2/00* (2006.01)
 *A61B 50/30* (2016.01)
 *A61B 90/00* (2016.01)

(52) U.S. Cl.
 CPC .... *A61B 17/06166* (2013.01); *A61B 50/3001* (2016.02); *A61B 90/39* (2016.02); *A61B 2017/06019* (2013.01); *A61B 2017/06042* (2013.01); *A61B 2017/06057* (2013.01); *A61B 2017/06076* (2013.01); *A61B 2017/06176* (2013.01); *A61F 2/0045* (2013.01); *A61F 2/0063* (2013.01)

(58) Field of Classification Search
 CPC ........ A61B 17/06166; A61B 17/06066; A61B 17/06171; A61B 2017/06171; A61B 2017/00663
 See application file for complete search history.

(56) References Cited

U.S. PATENT DOCUMENTS

| | | |
|---|---|---|
| 816,026 A | 3/1906 | Meier |
| 879,758 A | 2/1908 | Foster |
| 1,142,510 A | 6/1915 | Engle |
| 1,248,825 A | 12/1917 | Dederer |
| 1,321,011 A | 11/1919 | Cottes |
| 1,558,037 A | 10/1925 | Morton |
| 1,728,316 A | 9/1929 | Von Wachenfeldt |
| 1,886,721 A | 11/1932 | O'Brien |
| 2,094,578 A | 10/1937 | Blumenthal et al. |
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Garnder |
| 2,480,271 A | 8/1949 | Sumner |
| 2,572,936 A | 10/1951 | Kulp et al. |
| 2,684,070 A | 7/1954 | Kelsey |
| 2,736,964 A | 3/1956 | Lieberman |
| 2,779,083 A | 1/1957 | Enton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski et al. |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,082,523 A | 3/1963 | Modes et al. |
| 3,123,077 A | 3/1964 | Alcamo |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | LeRoy |
| 3,394,704 A | 7/1968 | Dery |
| 3,494,006 A | 2/1970 | Brumlik |
| 3,522,637 A | 8/1970 | Brumlik |
| 3,525,340 A | 8/1970 | Gilbert |
| 3,527,223 A | 9/1970 | Shein |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | de Mestral et al. |
| 3,748,701 A | 7/1973 | de Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,963,031 A | 6/1976 | Hunter |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,990,144 A | 11/1976 | Schwartz |
| 4,006,747 A | 2/1977 | Kronenthal |
| 4,008,303 A | 2/1977 | Glick et al. |
| 4,027,608 A | 6/1977 | Arbuckle |
| 4,043,344 A | 8/1977 | Landi |
| 4,052,988 A | 10/1977 | Doddi et al. |
| D246,911 S | 1/1978 | Bess, Jr. et al. |
| 4,069,825 A | 1/1978 | Akiyama |
| 4,073,298 A | 2/1978 | Le Roy |
| 4,137,921 A | 2/1979 | Okuzumi et al. |
| 4,159,686 A | 7/1979 | Heim |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A | 7/1981 | Wolosianski |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey |
| 4,434,796 A | 3/1984 | Karapetian |
| 4,449,298 A | 5/1984 | Patz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |

(56) References Cited

U.S. PATENT DOCUMENTS

| | | |
|---|---|---|
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,712,553 A | 12/1987 | MacGregor |
| 4,719,917 A | 1/1988 | Barrows |
| 4,741,330 A | 5/1988 | Hayhurst |
| 4,750,910 A | 6/1988 | Takayanagi et al. |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuck et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schultz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,102,418 A | 4/1992 | Granger et al. |
| 5,102,421 A | 4/1992 | Anpach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,387,227 A | 2/1995 | Grice |
| 5,391,173 A | 2/1995 | Wilk |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup, III et al. |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |

(56) References Cited

U.S. PATENT DOCUMENTS

| | | |
|---|---|---|
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,654 A | 9/1997 | Thompson |
| 5,662,714 A | 9/1997 | Charvin et al. |
| 5,669,935 A | 9/1997 | Rosenman et al. |
| 5,676,675 A | 10/1997 | Grice |
| D386,583 S | 11/1997 | Ferragamo et al. |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mullhauser et al. |
| 5,779,719 A | 7/1998 | Klein et al. |
| 5,782,864 A | 7/1998 | Lizardi |
| 5,807,403 A | 9/1998 | Bear et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,921,982 A | 7/1999 | Lesh et al. |
| 5,925,078 A | 7/1999 | Anderson |
| 5,931,855 A | 8/1999 | Buncke |
| 5,935,138 A | 8/1999 | McJames, II et al. |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 5,997,554 A | 12/1999 | Thompson |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,042,583 A | 3/2000 | Thompson et al. |
| 6,045,571 A | 4/2000 | Hill et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,245,091 B1 * | 6/2001 | Buncke ............... A61B 17/06 606/222 |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,095 B1 | 5/2002 | Kennett et al. |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,508,833 B2 | 1/2003 | Pavcnik et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,575,976 B2 | 3/2003 | Grafton |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,592,625 B2 | 7/2003 | Cauthen |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |

(56) References Cited

U.S. PATENT DOCUMENTS

| | | |
|---|---|---|
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,838 B2 | 3/2004 | D'Aversa et al. |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,723,107 B1 | 4/2004 | Skiba et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,756,000 B2 | 6/2004 | Antal et al. |
| 6,773,450 B2 | 8/2004 | Leung et al. |
| 6,776,340 B2 | 8/2004 | Murokh et al. |
| 6,776,789 B2 | 8/2004 | Bryant et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Ledlein et al. |
| 6,858,222 B2 | 2/2005 | Nelson et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,915,623 B2 | 7/2005 | Dey et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,951,565 B2 | 10/2005 | Keane et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,004,970 B2 | 2/2006 | Cauthen, III et al. |
| 7,021,316 B2 | 4/2006 | Leiboff |
| 7,026,437 B2 | 4/2006 | Shalaby et al. |
| 7,033,379 B2 | 4/2006 | Peterson |
| 7,037,984 B2 | 5/2006 | Ledlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,070,858 B2 | 7/2006 | Shalaby et al. |
| 7,074,117 B2 | 7/2006 | Dore |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,207 B2 | 9/2006 | Allen et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | Del Rio et al. |
| 7,150,712 B2 | 12/2006 | Buehlmann et al. |
| 7,150,757 B2 | 12/2006 | Fallin et al. |
| 7,152,605 B2 | 12/2006 | Khairkhahan et al. |
| 7,156,858 B2 | 1/2007 | Shuldt-Hempe et al. |
| 7,156,862 B2 | 1/2007 | Jacobs et al. |
| 7,160,312 B2 | 1/2007 | Saadat |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,294,357 B2 | 11/2007 | Roby |
| 7,297,142 B2 | 11/2007 | Brock |
| 7,322,105 B2 | 1/2008 | Lewis |
| 7,329,271 B2 | 2/2008 | Koyfman et al. |
| 7,351,250 B2 | 4/2008 | Zamierowski |
| 7,357,810 B2 | 4/2008 | Koyfman et al. |
| 7,371,253 B2 | 5/2008 | Leung et al. |
| 7,381,211 B2 | 6/2008 | Zamierowski |
| 7,387,634 B2 | 6/2008 | Benderev |
| 7,410,495 B2 | 8/2008 | Zamierowski |
| 7,413,570 B2 | 8/2008 | Zamierowski |
| 7,413,571 B2 | 8/2008 | Zamierowski |
| 7,416,556 B2 | 8/2008 | Jackson |
| 7,425,200 B2 | 9/2008 | Brockway et al. |
| 7,445,626 B2 | 11/2008 | Songer et al. |
| 7,452,371 B2 | 11/2008 | Pavcnik et al. |
| 7,467,710 B2 | 12/2008 | Cerwin et al. |
| 7,468,068 B2 | 12/2008 | Kolster |
| 7,481,826 B2 | 1/2009 | Cichocki, Jr. |
| 7,491,214 B2 | 2/2009 | Greene, Jr. et al. |
| 7,510,566 B2 | 3/2009 | Jacobs et al. |
| 7,513,904 B2 | 4/2009 | Sulamanidze et al. |
| 7,547,315 B2 | 6/2009 | Peterson et al. |
| 7,547,316 B2 | 6/2009 | Priewe et al. |
| 7,572,275 B2 | 8/2009 | Fallin et al. |
| 7,582,105 B2 | 9/2009 | Kolster |
| 7,591,850 B2 | 9/2009 | Cavazzoni |
| 7,601,164 B2 | 10/2009 | Wu |
| 7,611,521 B2 | 11/2009 | Lubbers et al. |
| 7,615,076 B2 | 11/2009 | Cauthen, III et al. |
| 7,624,487 B2 | 12/2009 | Trull et al. |
| 7,641,672 B2 | 1/2010 | Fallin et al. |
| 7,641,825 B2 | 1/2010 | Rizk |
| 7,645,293 B2 | 1/2010 | Martinek et al. |
| 7,678,134 B2 | 3/2010 | Schmieding et al. |
| 7,682,374 B2 | 3/2010 | Foerster et al. |
| 7,686,200 B2 | 3/2010 | Peterson |
| 7,691,112 B2 | 4/2010 | Chanduszko et al. |
| 7,708,759 B2 | 5/2010 | Lubbers et al. |
| 7,740,646 B2 | 6/2010 | Hunt et al. |
| 7,744,609 B2 | 6/2010 | Allen et al. |
| 7,758,595 B2 | 7/2010 | Allen et al. |
| 7,766,926 B2 | 8/2010 | Bosley, Jr. et al. |
| 7,766,939 B2 | 8/2010 | Yeung et al. |
| 7,803,574 B2 | 9/2010 | Desai et al. |
| 7,806,908 B2 | 10/2010 | Ruff |
| 7,815,589 B2 | 10/2010 | Meade et al. |
| 7,845,356 B2 | 12/2010 | Paraschac et al. |
| 7,850,894 B2 | 12/2010 | Lindh et al. |
| 7,857,829 B2 | 12/2010 | Kaplan et al. |
| 7,862,583 B2 | 1/2011 | Long |
| 7,871,425 B2 | 1/2011 | Jones et al. |
| 7,875,055 B2 | 1/2011 | Cichocki, Jr. |
| 7,879,072 B2 | 2/2011 | Bonutti et al. |
| 7,901,381 B2 | 3/2011 | Birk et al. |
| 7,913,365 B2 | 3/2011 | Genova et al. |
| 7,919,112 B2 | 4/2011 | Pathak et al. |
| 7,923,075 B2 | 4/2011 | Yeung et al. |

(56) References Cited

U.S. PATENT DOCUMENTS

| | | |
|---|---|---|
| 7,935,773 B2 | 5/2011 | Hadba et al. |
| 7,950,559 B2 | 5/2011 | Peterson et al. |
| 7,951,065 B2 | 5/2011 | Bosley, Jr. et al. |
| 7,956,100 B2 | 6/2011 | Wang |
| 7,967,841 B2 | 6/2011 | Yuan et al. |
| 7,972,347 B2 | 7/2011 | Garvin et al. |
| 7,981,140 B2 | 7/2011 | Burkhart |
| 7,996,967 B2 | 8/2011 | Genova et al. |
| 7,996,968 B2 | 8/2011 | Genova et al. |
| 8,011,072 B2 | 9/2011 | Genova et al. |
| 8,015,678 B2 | 9/2011 | Genova et al. |
| 8,016,881 B2 | 9/2011 | Furst |
| 8,020,263 B2 | 9/2011 | Genova et al. |
| 8,028,387 B2 | 10/2011 | Genova et al. |
| 8,028,388 B2 | 10/2011 | Genova et al. |
| 8,032,996 B2 | 10/2011 | Trull et al. |
| 8,056,599 B2 | 11/2011 | Maiorino |
| 8,062,654 B2 | 11/2011 | Nelson et al. |
| 8,066,736 B2 | 11/2011 | Peterson et al. |
| 8,074,654 B2 | 12/2011 | Paraschac et al. |
| 8,074,857 B2 | 12/2011 | Peterson et al. |
| 8,083,770 B2 | 12/2011 | Leung et al. |
| 8,097,005 B2 | 1/2012 | Cohn et al. |
| 8,100,940 B2 | 1/2012 | Leung et al. |
| 8,118,822 B2 | 2/2012 | Schaller et al. |
| 8,118,834 B1 | 2/2012 | Goraltchouk et al. |
| 8,128,393 B2 | 3/2012 | Rolland et al. |
| 8,151,661 B2 | 4/2012 | Schena et al. |
| 8,158,143 B2 | 4/2012 | Lendlein et al. |
| 8,161,618 B2 | 4/2012 | Maiorino et al. |
| 8,192,462 B2 * | 6/2012 | Sulamanidze ... A61B 17/06066 606/228 |
| 8,202,531 B2 | 6/2012 | McKay |
| 8,216,273 B1 | 7/2012 | Goraltchouk et al. |
| 8,222,564 B2 | 7/2012 | Maiorino et al. |
| 8,225,673 B2 | 7/2012 | D'Agostino |
| 8,226,684 B2 | 7/2012 | Nawrocki et al. |
| 8,236,027 B2 | 8/2012 | Wu |
| 8,246,652 B2 | 8/2012 | Ruff |
| 8,257,393 B2 | 9/2012 | Cichocki, Jr. |
| 8,267,961 B2 | 9/2012 | Popadiuk et al. |
| 8,273,105 B2 | 9/2012 | Cohen et al. |
| 8,287,555 B2 | 10/2012 | Starksen et al. |
| 8,303,625 B2 | 11/2012 | Lendlein et al. |
| 8,308,761 B2 | 11/2012 | Brailovski et al. |
| 8,353,931 B2 | 1/2013 | Stopek et al. |
| 8,403,017 B2 | 3/2013 | Maiorino et al. |
| 8,403,947 B2 | 3/2013 | Ochiai |
| 8,454,653 B2 | 6/2013 | Hadba et al. |
| 8,480,557 B2 | 7/2013 | Guterman |
| 8,500,762 B2 | 8/2013 | Sholev et al. |
| 8,541,027 B2 | 9/2013 | Wright et al. |
| 8,562,644 B2 | 10/2013 | Yuan et al. |
| 8,563,117 B2 | 10/2013 | Messersmith et al. |
| 8,615,856 B1 | 12/2013 | Gelbart |
| 8,628,465 B2 | 1/2014 | Mamo et al. |
| 8,641,732 B1 | 2/2014 | Goraltchouk et al. |
| 8,652,170 B2 | 2/2014 | Leung et al. |
| 8,652,215 B2 | 2/2014 | Bellamkonda et al. |
| 8,663,277 B2 | 3/2014 | Collier et al. |
| 8,673,536 B2 | 3/2014 | Lendlein et al. |
| 8,679,158 B2 | 3/2014 | Leung et al. |
| 8,690,914 B2 | 4/2014 | Leung et al. |
| 8,707,959 B2 | 4/2014 | Paraschac et al. |
| 8,721,664 B2 | 5/2014 | Ruff et al. |
| 8,721,681 B2 | 5/2014 | Ruff et al. |
| 8,734,485 B2 | 5/2014 | Leung et al. |
| 8,734,486 B2 | 5/2014 | Leung et al. |
| 8,793,863 B2 | 5/2014 | Hunter et al. |
| 8,747,436 B2 | 6/2014 | Nawrocki et al. |
| 8,747,437 B2 | 6/2014 | Leung et al. |
| 8,764,776 B2 | 7/2014 | Leung et al. |
| 8,764,796 B2 | 7/2014 | Kaplan et al. |
| 8,771,313 B2 | 7/2014 | Goraltchouk et al. |
| 8,777,987 B2 | 7/2014 | Herrmann et al. |
| 8,777,988 B2 | 7/2014 | Leung et al. |
| 8,777,989 B2 | 7/2014 | Leung et al. |
| 8,795,332 B2 | 8/2014 | Leung et al. |
| 8,821,539 B2 | 9/2014 | Rousseau |
| 8,821,540 B2 | 9/2014 | Leung et al. |
| 8,852,232 B2 | 10/2014 | Leung et al. |
| 8,864,776 B2 | 10/2014 | Bogart et al. |
| 8,870,916 B2 | 10/2014 | Ewers et al. |
| 8,875,607 B2 | 11/2014 | Kozlowski |
| 8,876,865 B2 | 11/2014 | Goraltchouk et al. |
| 8,888,796 B2 | 11/2014 | Lindh et al. |
| 8,888,810 B2 | 11/2014 | Hadba et al. |
| 8,915,943 B2 | 12/2014 | Hunter |
| 8,926,659 B2 | 1/2015 | Genova et al. |
| 8,932,327 B2 | 1/2015 | Kosa et al. |
| 8,932,328 B2 | 1/2015 | Megaro et al. |
| 8,944,804 B2 | 2/2015 | Robeson et al. |
| 8,961,560 B2 | 2/2015 | Avelar et al. |
| 9,011,489 B2 | 4/2015 | Ostrovsky et al. |
| 9,125,647 B2 | 9/2015 | Goraltchouk et al. |
| 9,138,222 B2 | 9/2015 | Bonutti et al. |
| 9,220,499 B2 | 12/2015 | Viola |
| 9,248,580 B2 | 2/2016 | Leung et al. |
| 9,307,983 B2 | 4/2016 | Stopek et al. |
| 9,398,943 B2 | 7/2016 | Criscuolo et al. |
| 9,439,746 B2 | 9/2016 | Bell et al. |
| 9,545,191 B2 | 1/2017 | Stokes et al. |
| 9,718,190 B2 | 8/2017 | Larkin et al. |
| 10,441,270 B2 | 10/2019 | Megaro et al. |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173822 A1 | 11/2002 | Justin et al. |
| 2003/0014077 A1 | 1/2003 | Leung et al. |
| 2003/0040795 A1 | 2/2003 | Elson et al. |
| 2003/0069602 A1 | 4/2003 | Jacobs et al. |
| 2003/0088270 A1 | 5/2003 | Lubbers et al. |
| 2003/0149447 A1 | 8/2003 | Morency |
| 2003/0167072 A1 | 9/2003 | Oberlander |
| 2003/0204193 A1 | 10/2003 | Gabriel et al. |
| 2004/0010275 A1 | 1/2004 | Jacobs et al. |
| 2004/0068293 A1 | 4/2004 | Scalzo et al. |
| 2004/0068294 A1 | 4/2004 | Scalzo et al. |
| 2004/0087970 A1 | 5/2004 | Chu |
| 2004/0087978 A1 | 5/2004 | Velez et al. |
| 2004/0088003 A1 | 5/2004 | Leung et al. |
| 2004/0098051 A1 | 5/2004 | Fallin et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0186487 A1 | 9/2004 | Klein et al. |
| 2004/0193257 A1 | 9/2004 | Wu et al. |
| 2004/0260340 A1 | 12/2004 | Jacobs et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0049636 A1 | 3/2005 | Leiboff |
| 2005/0055051 A1 | 3/2005 | Grafton |
| 2005/0065533 A1 | 3/2005 | Magen et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0154255 A1 | 7/2005 | Jacobs |
| 2005/0181009 A1 | 8/2005 | Hunter et al. |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0267531 A1 | 12/2005 | Ruff et al. |

(56) References Cited

U.S. PATENT DOCUMENTS

| | | |
|---|---|---|
| 2006/0020272 A1 | 1/2006 | Gildenberg |
| 2006/0036266 A1 | 2/2006 | Sulamanidze et al. |
| 2006/0058799 A1 | 3/2006 | Elson et al. |
| 2006/0058844 A1 | 3/2006 | White et al. |
| 2006/0079469 A1 | 4/2006 | Anderson et al. |
| 2006/0085016 A1 | 4/2006 | Eremia |
| 2006/0089672 A1 | 4/2006 | Martinek |
| 2006/0111742 A1 | 5/2006 | Kaplan et al. |
| 2006/0116503 A1 | 6/2006 | Lendlein et al. |
| 2006/0135994 A1 | 6/2006 | Ruff |
| 2006/0135995 A1 | 6/2006 | Ruff |
| 2006/0142784 A1 | 6/2006 | Kontos |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235447 A1 | 10/2006 | Walshe |
| 2006/0241658 A1 | 10/2006 | Cerundolo |
| 2006/0253126 A1 | 11/2006 | Bjerken et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2007/0016251 A1 | 1/2007 | Roby |
| 2007/0027475 A1 | 2/2007 | Pagedas |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0151961 A1 | 7/2007 | Kleine et al. |
| 2007/0156175 A1 | 7/2007 | Weadock et al. |
| 2007/0208355 A1 | 9/2007 | Ruff |
| 2007/0213770 A1 | 9/2007 | Drefyss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0239206 A1 | 10/2007 | Shelton, IV et al. |
| 2007/0239207 A1 | 10/2007 | Beramendi |
| 2007/0293892 A1 | 12/2007 | Takasu |
| 2008/0009902 A1 | 1/2008 | Hunter et al. |
| 2008/0046094 A1 | 2/2008 | Han et al. |
| 2008/0066764 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0132943 A1 | 6/2008 | Maiorino et al. |
| 2008/0195147 A1 | 8/2008 | Stopek |
| 2008/0215072 A1 | 9/2008 | Kelly |
| 2008/0221618 A1 | 9/2008 | Chen et al. |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2009/0018577 A1 | 1/2009 | Leung et al. |
| 2009/0082856 A1 | 3/2009 | Flanagan |
| 2009/0099597 A1 | 4/2009 | Isse |
| 2009/0105753 A1 | 4/2009 | Greenhalgh et al. |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0226500 A1 | 9/2009 | Avelar et al. |
| 2009/0228021 A1 | 9/2009 | Leung |
| 2009/0248066 A1 | 10/2009 | Wilkie |
| 2009/0248070 A1 | 10/2009 | Kosa et al. |
| 2009/0259251 A1 | 10/2009 | Cohen |
| 2009/0299408 A1 | 12/2009 | Schuldt-Hempe et al. |
| 2010/0057123 A1 | 3/2010 | D'Agostino et al. |
| 2010/0063540 A1 | 3/2010 | Maiorino |
| 2010/0163056 A1 | 7/2010 | schopp et al. |
| 2010/0239635 A1 | 9/2010 | McClain et al. |
| 2010/0298637 A1 | 11/2010 | Ruff |
| 2010/0298867 A1 | 11/2010 | Ruff |
| 2010/0298868 A1 | 11/2010 | Ruff |
| 2010/0298871 A1 | 11/2010 | Ruff et al. |
| 2010/0313729 A1 | 12/2010 | Genova et al. |
| 2010/0318123 A1 | 12/2010 | Leung et al. |
| 2011/0022086 A1 | 1/2011 | D'Agostino et al. |
| 2011/0125188 A1 | 5/2011 | Goraltchouk et al. |
| 2011/0264138 A1 | 10/2011 | Avelar et al. |

FOREIGN PATENT DOCUMENTS

| | | |
|---|---|---|
| CN | 2640420 | 9/2004 |
| DE | 628038 | 3/1936 |
| DE | 1810800 | 6/1970 |
| DE | 3227984 | 2/1984 |
| DE | 4302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0428253 | 5/1991 |
| EP | 0464479 | 1/1992 |
| EP | 0464480 | 1/1992 |
| EP | 0513713 | 5/1992 |
| EP | 0513736 | 11/1992 |
| EP | 0558993 | 9/1993 |
| EP | 0574707 | 12/1993 |
| EP | 0576337 | 12/1993 |
| EP | 0612504 | 8/1994 |
| EP | 0632999 | 1/1995 |
| EP | 0664198 | 7/1995 |
| EP | 0668056 | 8/1995 |
| EP | 0673624 | 9/1995 |
| EP | 0705567 | 4/1996 |
| EP | 0755656 | 1/1997 |
| EP | 0826337 | 3/1998 |
| EP | 0839499 | 5/1998 |
| EP | 0913123 | 5/1999 |
| EP | 0916310 | 5/1999 |
| EP | 0960600 | 12/1999 |
| EP | 1075843 | 2/2005 |
| EP | 1525851 | 4/2005 |
| EP | 1532942 | 5/2005 |
| EP | 0991359 | 11/2007 |
| EP | 2036502 | 3/2009 |
| EP | 1948261 | 11/2010 |
| EP | 1726317 | 7/2012 |
| FR | 401199 A | 8/1909 |
| FR | 2619129 | 2/1989 |
| FR | 2693108 | 1/1994 |
| GB | 267007 | 3/1927 |
| GB | 1091282 | 11/1967 |
| GB | 1428560 | 3/1976 |
| GB | 1506362 | 4/1978 |
| GB | 1508627 | 4/1978 |
| JP | S54-116419 | 9/1979 |
| JP | S63-288146 | 11/1988 |
| JP | H01-113091 | 5/1989 |
| JP | H03-165751 | 7/1991 |
| JP | H04-96758 | 3/1992 |
| JP | H04-266749 | 9/1992 |
| JP | H09-103477 | 4/1997 |
| JP | H10-85225 | 4/1998 |
| JP | H11-313826 | 11/1999 |
| JP | H11-332828 | 12/1999 |
| JP | 2002-059235 | 2/2002 |
| JP | 2003-275217 | 9/2003 |
| JP | 2009-118967 | 6/2009 |
| KR | 2005-0072908 | 7/2005 |
| KR | 2006-0013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 | 1/2006 |

(56) References Cited

FOREIGN PATENT DOCUMENTS

| | | |
|---|---|---|
| SU | 1745214 | 7/1992 |
| SU | 1752358 | 8/1992 |
| WO | WO 1996/006565 | 3/1966 |
| WO | WO 1986/000020 | 1/1986 |
| WO | WO 1987/001270 | 3/1987 |
| WO | WO 1988/009157 | 12/1988 |
| WO | WO 1989/005618 | 6/1989 |
| WO | WO 1990/009149 | 8/1990 |
| WO | WO 1990/014795 | 12/1990 |
| WO | WO 1992/022336 | 12/1992 |
| WO | WO 1995/016399 | 6/1995 |
| WO | WO 1995/029637 | 11/1995 |
| WO | WO 1997/000047 | 1/1997 |
| WO | WO 1998/052473 | 11/1998 |
| WO | WO 1998/055031 | 12/1998 |
| WO | WO 1999/021488 | 5/1999 |
| WO | WO 1999/033401 | 7/1999 |
| WO | WO 1999/052478 | 10/1999 |
| WO | WO 1999/059477 | 11/1999 |
| WO | WO 1999/062431 | 12/1999 |
| WO | WO 2000/051658 | 9/2000 |
| WO | WO 2000/051685 | 9/2000 |
| WO | WO 2001/006952 | 2/2001 |
| WO | WO 2001/056626 | 8/2001 |
| WO | WO 2003/001979 | 1/2003 |
| WO | WO 2003/002027 | 1/2003 |
| WO | WO 2003/003925 | 1/2003 |
| WO | WO 2003/045255 | 6/2003 |
| WO | WO 2003/077772 | 9/2003 |
| WO | WO 2003/092758 | 11/2003 |
| WO | WO 2003/103733 | 12/2003 |
| WO | WO 2003/103972 | 12/2003 |
| WO | WO 2003/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2007/145614 | 12/2007 |
| WO | WO 2008/014491 | 1/2008 |
| WO | WO 2008/107919 | 9/2008 |
| WO | WO 2008/128113 | 10/2008 |
| WO | WO 2008/136549 | 11/2008 |
| WO | WO 2008/141034 | 11/2008 |
| WO | WO 2008/150773 | 12/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO 2009/151876 | 12/2009 |
| WO | WO 2010/052007 | 5/2010 |
| WO | WO 2011/053375 | 5/2011 |
| WO | WO 2011/139916 | 11/2011 |
| WO | WO 2011/140283 | 11/2011 |

OTHER PUBLICATIONS

European Communication dated Sep. 27, 2019 for Application No. 18187211.0, 4 pages.
European Communication dated Apr. 22, 2020 for Application No. 18187211.0, 5 pages.
Bacci, Pier Antonio, "Chirurgia Estetica Mini Invasiva Con Fili Di Sostegno", Collana di Arti, Pensiero e Scienza; Minelli Editore—2006; 54 pgs.
Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Bellin, I. et al., "Polymeric triple-shape materials", Proceedings of the National Academy of Sciences of the United States of America Nov. 28, 2006; 2103(48):18043-18047.
Boenisch, U.W. et al. 'Pull-Out strength and stiffness of meniscal repair using absorbable arrows or Ti-Cron vertical and horizontal loop sutures' American Journal of Sports Medicine, Sep.-Oct. (1999) vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al. 'The Suture Repair of One-Millimeter Vessels, microvascular surgery' (1966) Report of First Conference; Oct. 6-7 pp. 24-35.
Bunnell, S. 'Gig pull-out suture for tendons' J Bone Joint Surg. Am (1954) vol. 36A, No. 4 pp. 850-851.
CCPR Centro De Cirurgia Plastica e Reabilitacao 'Up Liftinig (Aptos Threads) http://ccpr.com.br/up1-1.htm, Aug. 19, 2002 pp. 1-2.
Dahlin, Lars, "Techniques of Peripheral Nerve Repair",Scandinavian Journal of Surgery 97: 310-316, 2008.
Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.
Datillo, Jr. P.P. et al. 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al. 'Tissue holding performance of knotless absorbable sutures'Society for Biomaterials 29th Annual Meeting Transactions (2003) p. 101.
Declaration of Dr. Gregory L. Ruff, dated Aug. 19, 2005, 8 pages, with Exhibits A-E.
De Persia, Raul et al., "Mechanics of Biomaterials: Sutures After Surgery", Applications of Engineering Mechanics in Medicine, GED-University of Puerto Rico, Mayaguez May 2005, p. F1-F27.
Delorenzi, C.L., "Barbed Sutures: Rationale and Technique", Aesthetic Surg. J. Mar. 26, 2006(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 27, 2006(2): 2 pages.
Gross, R.A. et al. 'Biodegradable Polymers for the Environment' Science (2002) vol. 297, Issue 5582 pp. 803.
Han, H. et al. 'Mating and Piercing Micromechanical Suture for Surface Bonding Applications' (1991) Proceedings of the 1991 Micro Electromechanical Systems (NIEMS>91), An Investigation of Microstructures, Sensors, Actuators, Machines and Robots pp. 253-258.

(56) References Cited

OTHER PUBLICATIONS

Ingle, N.P. et al. 'Barbed Suture Anchoring Strength: Applicability to Dissimilar Polymeric Materials' College of Textiles, North Carolina State University, 7th World Biomaterials Congress 2004, 1 page.
Ingle, N.P. et al. 'Mechanical Performance and Finite Element Analysis of Bidirectional Barbed Sutures' Master of Science in Textile Technology & Management at North Carolina State University Aug. 2003, 126 pages.
Ingle, N.P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.
Jennings et al. 'A New Technique in primary tendon repair' Surg. Gynecol. Obstet. (1952) vol. 95, No. 5 pp. 597-600.
Jeong, H.E. et al. 'A nontransferring dry adhesive with hierarchal polymer nanohairs' PNAS 106 (14) pp. 5639-5644 (2009).
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio [(ε-hydroxycaproate)-co-glycolate] dimethacrylates and Butyl Acrylate with Adjustable Hydrolytic Degradation Rate", Biomacromolecules 2007;8(3):10181027.
Khademhosseini, Ali et al., "Nanobiotechnology Drug Delivery and Tissue Engineering", Chemical Engineering Progress 102:38-42 (2006).
Kuniholm J.F. et al. 'Automated Knot Tying for Fixation in Minimally Invasive, Robot Assisted Cardiac Surgery' Master of Science in Mechanical & Aerospace Engineering at North Carolina State University May 2003, 71 pages.
Lendlein, A. et al. 'Biodegradable, Elastic Shape-Memory Polymers for Potential Biomedical Applications' (2002) Science vol. 296 pp. 1673-1676.
Lendlein, A. et al. 'Shape-Memory Polymers' Agnew Chem. Int. Ed. (2002) vol. 41 pp. 2034-2057.
Leung, J. et al. 'Barbed, Bi-directional Medical Sutures: Biomechanical Properties and Wound Closure Efficacy Study' 2002 Society for Biomaterials 28the Annual Meeting Transactions 1 page.
Leung, J. et al. 'Barbed, Bi-directional Surgical Sutures' International Conference & Exhibition on Healthcare & Medical Textiles, Jul. 8-9, 2003 pp. 1-8.
Leung, J. et al. 'Barbed, Bi-directional Surgical Sutures: In Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Leung, J. et al. 'Performance Enhancement of a Knotless Suture via Barb Geometry Modifications' 7th World Biomaterials Congress 2004, 1 page.
Li, Y.Y. et al. 'Polymer Replicas of Photonic Porous Silicon for Sensing and Drug Delivery Applications' (2003) Science vol. 299 pp. 2045-2047.
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas et al., "Neurotrophic factors release from nerve conduits for peripheral axonal regeneration", European Cells and Materials vol. 16; Suppl. 1 (2008), p. 14.
Madhave et al. 'A biodegradable and biocompatible gecko-inspired tissue adhesive' PNAS 105(7) pp. 2307-2312 (2008).
Maitland et al., "Prototype laser-activated shape memory polymer foam device for embolic treatment of aneurysms", Journal of Biomedical Optics May/Jun. 2007;12(3): pp. 030504-1 to 030504-3.

Malina, M. et al. 'Endovascular AAA Exlusion: Will Stents with Hooks and Barbs Prevent Stent-Graft Migration' Journal Endovascular Surgery (1998) vol. 5 pp. 310-317.
Mansberger et al. 'A New Type Pull-Out Wire for Tendon Surgery: A Preliminary Report' Department of Surgery, University Hospital and Univeristy of Maryland School of Medicine, Baltimore, Maryland, Received for Publication May 10, 1951 pp. 119-121.
Martin, D.P. et al. 'Medical applications of poly-4-hydroxybuturate: a strong flexible absorbable biomaterial' Biochemical Engineering Journal vol. 16 (2003) pp. 97-105.
Mason, M.L. 'Primary and Secondary Tendon Suture. A discussion of the significance of technique in tendon surgery' (1940) Surg Gynecol Obstet 70.
Mckee, GK 'Metal anastomosis tubes in tendon suture' The Lancet (1945) pp. 659-660.
Mckenzie 'An Experimental Multiple Barbed Suture for the Long Flexor Tendons of the Palm and Fingers' The Journal of Bone and Joint Surgery (1967) vol. 49B, No. 3 pp. 440-447.
Middleton and Tipton 'Synthetic Biodegradable Polymers as Medical Devices' (1998) Medical Plastics and 13iomaterial s Magazine, 9 pages.
Moran et al., "Bidirectional-Barbed Sutured Knotless Running Anastomosis v Classic van Velthovan in a Model System", Journal of Endourology Oct. 2007; 21(10); 1175-1177.
Mullner, "Metal Foam Has a Good Memory", Dec. 18, 2007 Original story at http://www.physorg.com/news117214996.html.
Murtha et al., "Evaluation of a Novel Technique for Wound Closure Using a Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D., "Bidirectional Barbed Sutures for Wound Closure: Evolution and Applications", Journal of the American College of Certified Wound Specialists (2009) 1, 51-57.
Paul, Malcolm D. and Rui Avelar, "Quill™ SRS Techniques & Procedures A Novel Approach to Soft Tissue Approximation", Canada, Angiotech Pharmaceuticals, Inc., First Edition Aug. 2007: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Second Edition Aug. 2008: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Third Edition 2009, 8 2007-2009: 27 pages.
Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, 8 2007-2010: 27 pages.
Paul, Malcolm D., "Using Barbed Sutures in Open/Subperiosteal Midface Lifting", Aesthetic Surgery Journal 2006(26): 725-732.
Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.
Quill Medical, Inc. 'Barbed Sutures, wrinkle filters give patients more innovative, non-surgical options' Press Release of Program presented at American Society of Plastic Surgeons annual scientific meeting; Philadephia, Oct. 9, 2004 3 pages.
Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Richert, Ludovic et al., "Surface Nanopatterning to Control Cell Growth", Advanced Materials 2008(15): 1-5.
Rodeheaver, G.T. et al., "Barbed Sutures for Wound Closure: In Vivo Wound Security, Tissue Compatibility and Cosmesis Measurements", Society for I3iomaterials 30th Annual Meeting Transactions, 2005, 2 pages.

(56) References Cited

OTHER PUBLICATIONS

Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects—Influence of suture numbers and reconstruction of nerve bifurcations", Restorative Neurology and Neuroscience 23 (2005) 79-85.
Schmid A. et al. 'The outspreading anchor cord. A material for arthoscopic suturing of a fresh anterior cruciate ligament rupture' Surgical Clinic of teh University of Gottingen' (1987) pp. 417-426.
Semenov, G.M. et al. 'Surgical Suture' (2001) Piter, Saint Petersburg, pp. 12-13 and 92-98.
Serafetinides, AA 'Short pulse laer beam interactions with polymers biocompatible materials and tissue' Proce SPIE vol. 3052 (1996) pp. 111-123.
Sulamanidze, M. et al., "APTOS Suture Lifting Methods: 10 Years of Experience", Cl in Plastic Surg 36 (2009); pp. 281-306.
Sulamanidze, M.A. et al. 'Clinical aspects of blodless facelift using APTOS filaments' A.V. Vishncvsky Institute of Surgery, Bol'shaya Scrpukhovskaya ul, 7, 113811, Moscow, Russia (2002) pp. 24-34.
Sulamanidze, M.A. et al. 'Facial lifting with Aptos threads' International Journal of Cosmetic Surgery and Aesthetic Dermatology' (2001) No. 4, pp. 1-8.
Sulamanidze, M.A. et al. 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al. 'Morphological foundations of facelift using APTOS filaments' Bolshaya Serpukhovskaya ul 27, 113811 Moscow, Russia (2002) pp. 19-26.
Sulamanidze, M.A. et al. 'Removal of Facial Soft Tissue Ptosis with Special Threads' Dermatol Surg (2002) vol. 28 pp. 367-371.
Sulamanidze, MD, M.A. et al., "Soft tissue lifting in the mid-face: old philosophy, new approach-internal stitching technique (APTOS Needle)", Plastic and Aesthetic Surgery Clinic Total SHARM, Moscow, Russia, (2005):15-29.
Sulzle, Inc. B.G. et al. Drilled End Surgical Needles Jul. 2002 Syracuse, New York.
Surgical Specialties Corporation, "Wound Closure Catalog"; Summer 2005, 5 pages.
Szarmach, R. et al. 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
Australian Office Action, Patent Examination Report No. 1, dated Oct. 17, 2013 for Application No. AU 2009319965, 5 pgs.
Australian Office Action, Patent Examination Report No. 2, dated Apr. 14, 2014 for Application No. AU 2009319965, 4 pgs.
Australian Office Action, Patent Examination Report No. 1, dated Jan. 12, 2016 for Application No. AU 2014253483, 5 pgs.
Canadian Office Action dated Sep. 17, 2015 for Application No. CA 2,742,506, 3 pgs.
Communication from EPO re: EP10000486 dated Apr. 4, 2011, 4 pages.
European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 2, 2007, 2 pages.
European Search Report for EP07016222 dated Jan. 7, 2008.
European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report re: EP10004453 dated Jun. 15, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10011872 dated Apr. 20, 2011.
European Search Report for EP10012437 dated Apr. 28, 2011.
European Search Report for EP10186592.1 dated Jan. 19, 2011, 2 pages.
European Search Report for EP10184766 dated Apr. 20, 2011.
European Office Action, Supplementary Partial European Search Report, dated Nov. 23, 2015 for Application No. EP 09829674.2, 9 pgs.
European Office Action, Supplementary European Search Report and Written Opinion dated Mar. 10, 2016 for Application No. EP 09829674.2, 14 pgs.
European Exam Report dated Aug. 17, 2017 for Application No. 09829674.2, 6 pgs.
European Search Report and Written Opinion dated Sep. 27, 2018 for Application No. EP 18187211.0, 7 pgs.
Partial European Search Report re: EP05025816 dated Mar. 20, 2006.
Extended European Search Report re: EP07015905.8 dated Oct. 23, 2007.
Extended European Search Report re: EP07016222.7 dated Jan. 30, 2008.
Supplementary European Search Report re: EP98923664 dated Jun. 12, 2001.
Supplementary European Search Report re: EP03752630 dated Nov. 17, 2005.
Supplementary European Search Report re: EP03770556 dated Nov. 17, 2005.
Supplementary European Search Report re: EP03754965 dated Nov. 18, 2005.
Supplementary European Search Report re: EP03785177 dated May 19, 2009.
Supplementarry European Search Report re: EP05750101 dated Apr. 7, 2010.
Supplementary European Search Report re: EP07017663 dated Nov. 7, 2007.
Indian Office Action and Search Report dated Jul. 4, 2018 for Application No. IN 3740/CHENP/2011, 5 pgs.
International Search Report for PCT/US1994/09631 dated Dec. 9, 1994.
International Search Report for PCT/US1998/10478 dated Sep. 23, 1998.
International Search Report for PCT/US2002/20449 dated May 20, 2003.
International Search Report for PCT/US2002/027525 dated Dec. 9, 2002, 3 pgs.
International Search Report for PCT/US2003/030424 dated Nov. 1, 2004.
International Search Report for PCT/US2003/030664 dated May 25, 2004.
International Search Report for PCT/US2003/030666 dated Dec. 15, 2004.
International Search Report for PCT/US2003/025088 dated Dec. 29, 2003.
International Search Report for: PCT/US2003/030674 dated Sep. 2, 2004.
International Search Report for: PCT/US2004/014962 dated Feb. 24, 2005.
International Search Report for PCT/US2005/017028 dated Mar. 26, 2008.

(56) References Cited

OTHER PUBLICATIONS

International Search Report for PCT/US2007/002688 dated Oct. 22, 2007.
International Search Report for PCT/US2007/074658 dated Jun. 12, 2007, 3 pgs.
International Search Report for PCT/US2008/060127 dated Sep. 23, 2008, 5 pgs.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/040545 dated Oct. 29, 2009.
International Search Report for PCT/US2009/041685 dated Dec. 22, 2009.
International Search Report for PCT/US2009/044274 dated Jan. 15, 2010.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report for: PCT/US2011/035431 dated Jan. 12, 2012.
International Search Report for PCT/US2011/059238 dated May 21, 2012.
Internatioanl Search Report for PCT/US2012/030441 dated Sep. 27, 2012.
International Search Report for PCT/US2012/041001 dated Sep. 26, 2012.
International Search Report for PCT/US2009/063081 dated Aug. 2, 2010.
Written Opinion of the International Searching Authority for PCT/US2009/063081, dated Aug. 2, 2010.
International Preliminary Report re: PCT/US1998/010478 dated Dec. 11, 1999.
International Preliminary Report re: PCT/US2007/002688 dated Aug. 14, 2008.
International Preliminary Report re: PCT/US2008/060127 dated Oct. 13, 2009.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2009/044274 dated Nov. 17, 2010.
International Preliminary Report re: PCT/US2011/035431 dated Nov. 6, 2012.
International Preliminary Report re: PCT/US2011/059238 dated May 7, 2013.
Mexican Office Action dated Feb. 11, 2015 for Application No. MX/a/2011/004688, 5 pgs.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Singapore Office Action dated Feb. 20, 2013 for Application No. SG 201103117-6, 10 pgs.
Singapore Search Report for Singapore Patent Application No. 201103117-6 dated Mar. 8, 2013.
Singapore Search Report for Singapore Patent Application No. 201308107-0 dated Jan. 22, 2016, 6 pages.

\* cited by examiner

LENGTH OF SELF-RETAINING SUTURE AND METHOD AND DEVICE FOR USING THE SAME

This application is a continuation of U.S. patent application Ser. No. 14/570,066 filed Dec. 15, 2014, now U.S. Pat. No. 10,441,270 issued Oct. 15, 2019, which is a continuation of U.S. patent application Ser. No. 13/127,220 filed Dec. 20, 2011, now U.S. Pat. No. 8,932,328 issued Oct. 13, 2015, which is a national stage entry of PCT/US09/63081 filed Nov. 3, 2009, now WO 2010/062743, published Jun. 3, 2010, which claims the priority to U.S. Provisional Pat. App. No. 61/110,952, filed Nov. 3, 2008.

BACKGROUND OF INVENTION

The present invention relates generally to an improved length of self-retaining suture and, more particularly, relates to converging sections of self-retaining suture as well as the method and device for using the same.

Self-retaining sutures have been used in the past in many different surgical applications. Self-retaining sutures have been shown to perform particularly well in binding together various body parts such as skin, muscle tissue, organs, blood vessels, tendons, organs and the like. Self-retaining sutures are advantageous to the surgical team because they provide an effective ligature of tissue without the requirement of an anchoring suture knot which can be difficult to tie and which can cause damage to tissue during the wound healing process. Self-retaining sutures also simplify many tissue repair applications by more evenly distributing repair retention forces along the length of the suture. The optimization of self-retaining sutures is disclosed in detail in U.S. Patent Publication US 2004/0060409A, issued as U.S. Pat. No. 8,100,940 on Jan. 24, 2012 and is incorporated herein in its entirety.

Typically, self-retaining sutures have been used to bind mammalian body parts together by passing a first length of self-retaining suture through a first section of tissue to be bound in a direction in which the retainers may pass relatively freely in one direction through the tissue, but will resist movement if the suture is moved in the direction opposed to the insertion direction. Then a second length of suture is passed through a second section of tissue in a second direction. Finally, the surgeon joins the two lengths together by tying them or otherwise binding them together.

One alternative method for use of a self-retaining suture is to use a single length of rigid self-retaining suture having a first end, a second end and the retainers disposed on the length of the suture in a bidirectional fashion. A portion of the length of the suture has retainers facing a first end and a portion of the length of the suture has retainers facing the second end. The suture binds tissue together by inserting the first end in a first section of tissue and inserting the second end in a second section of tissue. The diverging retainers resisted movement of the sections away from the wound and help bind them together. This retainer design and methodology is disclosed more fully in U.S. Patent 6,241,74781 and is incorporated herein in its entirety.

Further, there are devices for use in inserting self-retaining sutures into the body of a mammal. These include tubular instruments having a hollow portion for holding a length of self-retaining suture. The end of the instrument includes a holding point for a pointed first end of the suture length and the front of the instrument includes a handle. In use, the end of the instrument is inserted into the body of a mammal at the point. The instrument, guided by the user holding it at the handle, is inserted along a pathway through an incision or wound for closure and up through the tissue, or the like, where the pointed end can clear the subject tissue. The user, while holding the pointed end, reverses direction along the insertion pathway with the instrument. This releases the length of suture within the instrument and enables the retainers to grasp the surrounding tissue. The instrument clears the wound area and the retainers holding the surrounding tissue keep the wound closed. Such a device is disclosed in U.S. Pat. No. 5,342,376.

Other self-retaining suture technologies are known to the applicants. Table 1 summarizes applicable self-retaining suture technology. Table 1 is attached and, along with its foreign counterparts and any continuations and/or divisionals, is incorporated herein by reference in its entirety.

In spite of the advances made to date relating to self-retaining suture technology, there does not exist a suture length made up of one or more sections containing converging retainer patterns that facilitates the placement of a suture without an attached needle. Such placement would be advantageous in several surgical tissue repair applications wherein the location of the tissue to be repaired constrains the passage and retrieval of an attached suture insertion device or where adjacent tissues could be harmed by the passage of the attached needle such as the passage of a needle past the bladder during the placement of a bladder neck suspension sling. Further, such placement would be useful in certain cases where robotic or other mechanically assisted surgical methods are employed in which simplified suture anchoring methods are desired. Also, such placement would be advantageous in fixing therapeutic devices to delicate tissues such as tumors in which such devices would operate more effectively if they were placed with minimal tissue disruption and if such therapeutic devices were immobilized during the period of therapeutic treatment. Also, such placement reduces the number of attached needles that must be retrieved from the surgical tissue. Thus reducing the established risk of inadvertently leaving needles in the patient after surgery is completed. Further, the manipulation of needles during this process of thread passage and needle retrieval is a well known risk for "needle stick" to the operator that can lead to the transmission of blood borne pathogens such as HIV and hepatitis.

At present, there does not exist any system or method where a length of suture is inserted with a detachable suture insertion device where the suture insertion device may be easily retracted along the needle's insertion pathway. Presently, after tissue or the like is anchored, the surgeon in some cases must continue to move the suture insertion device further through tissue to retrieve the needle. This may result in further damage to the tissue, as discussed above. When the surgeon moves the suture insertion device further through tissue to enable the suture insertion device to exit the body, this also results in the formation of a suture insertion-device-exiting-pathway which creates an opportunity for the suture to migrate from its initial placement position Such migration can lead to movement of the anchored tissue or disconnection of joined tissues relative to each other. Such movement could lead to complete or partial failure of the procedure. Also, the suture itself may migrate into positions that are harmful to adjacent tissue and organs.

A further disadvantage of the present state of the art is that the area tissue surrounding the suture placement may become damaged during the procedure because of the surgeon's need to retrieve the attached needle. Presently, a surgeon must not only insert a suture and any attachment to the desired location, but to retrieve the needle, the surgeon must move the needle through a particular area of tissue to enable the needle to exit. Alternatively, the surgeon may choose to try to reverse the attached needle's pathway at the point of suture placement. In either case, there can be significant disruption to the tissue in the surrounding area. This can become a critical issue where the surgeon is working in the area of a cancerous tumor. If the tumor becomes damaged or as a result of the disruption to tissue, the procedure is ineffective, the cancer may spread or the procedure to treat the cancer may fail. Thus, there is no system or method of placing a suture at a desired location that leaves the surrounding tissue unharmed and undamaged.

Another disadvantage of the present state of art relates to surgical procedures that require a significantly deep incision relative to the size of the incision at the skin level. In particular, endoscopic procedures and surgeries often require minimum incisions at the skin level and yet may be quite deep. As a result, it is often difficult for the surgeon to work in such a cramped environment. Closing this access port is challenging to do with conventional attached needles, especially at the deepest portion s of the narrow opening where there is little room to manipulate a needle driver and forceps to grasp and retrieve an attached needle.

One version of a converging self-retaining suture pattern is in a suture length made up of a continuous loop having converging retainers along at least a portion of the length, wherein the loop is inserted into a section of tissue to support a body part of a mammal. Further, there is no method or device at present that enables a user to accurately and effectively insert a looped length of self-retaining suture into the body of a mammal where the insertion end of the suture length remains within the body of a mammal without the need for holding, joining or pulling on the insertion end of the suture. Such a method or a device would enable a surgeon or other medical personnel to engage in procedures that would deliver more effective treatment to patients while minimizing damage to the surrounding tissue. This would provide greater success rates of certain procedures, decrease recovery time, minimize complications and thus decrease the overall cost to perform such procedures.

Accordingly, it is desired to provide a continuous loop of suture having converging retainers on at least a portion of its length where the loop is inserted into the body of a mammal to support a body part.

It is further desired to provide a method and device for inserting a length of suture having converging retainers along at least a portion thereon, where the inserted end remains within the body of the mammal and does not need to be pulled or manually held or joined to another length thereof.

It is yet further desired to provide a method of support a body part of a mammal by inserting a length of suture having retainers along at least a portion thereof, where the length of suture remains within the insertion pathway and the insertion end of the suture does not need to be held or, joined to another length of suture or pulled clear of insertion area for the method to be effective.

It is still further desired to provide a method and device for supporting a body part of a mammal where the length of suture is inserted into the body of mammal at a point that ensures significant effectiveness in the continued support of the body part.

It is yet further desired to provide a method and device for supporting a body part of a mammal where the procedure is minimally invasive, minimizes damage to the body during the procedure recovery time and reduces the overall cost of performing the procedure.

It is yet further desired to provide a method and device for placing sutures in tissue where the procedure is minimally invasive, minimizes damage to the body during the repair procedure, minimizes recovery time and reduces the overall costs of performing the procedure.

It is still further desired to provide a method and device for placing sutures in tissue where the suture is easily detached from the suture insertion device and the suture insertion device is able to be retracted from the tissue by reversing its travel along the insertion pathway.

It is yet further desired to provide a method and device for anchoring a length of suture in a particular location in tissue in such a manner that minimizes the possibility for suture migration and for damage to surrounding tissue.

It is further desired to provide a method and device for anchoring a suture and attachment such as a marker, tack, tag, chemotherapeutic drug delivery agent, seroma evacuation tube or the like into the tissue with great accuracy and with minimal disruption to surrounding tissue.

It is also desired to provide a method and system for ensuring that all needles used in a surgical procedure are retrieved.

BRIEF SUMMARY OF INVENTION

The present invention provides for a suture having an elongated body having a first end, a second end, and a plurality of retainers projecting from the body. The retainers are disposed on the periphery of the body along at least a portion of the length of the body. All of the retainers face the first end. The retainers are configured such that when the length of suture is inserted into the tissue of a mammal the retainers generally flex toward the body during insertion where damage to the tissue by the retainers is minimized, and the retainers generally resist movement when the suture is pulled in a direction opposed to the insertion pathway. The suture also has a temporary holding point for an insertion device to hold the body. The point is located proximate to the first end.

The present invention also provides for a continuous length of suture where the ends are joined together to form a loop. The loop has a first length of suture having an elongate first body. A plurality of first retainers project from the first body in a first direction. The first retainers are disposed on the periphery of the first body along at least a portion of the first length. The loop also has a second length having a plurality of second retainers projecting from the second body in a second direction, the second direction being opposite to the first direction. The second retainers are disposed on the periphery of the second body along at least a portion of the second length. The loop has an intervening length located between the first and second lengths, whereby all of the first retainers and all of the second retainers face the intervening length.

The present invention further provides for a continuous length of suture where the ends are joined together to form a loop. The loop has a first half having an elongate first half body having a first section, a second section and a first intervening section. A plurality of first retainers project peripherally from the first section along at least a portion thereof, in a first direction. A plurality of second retainers project peripherally from the second section along at least a portion thereof in a direction opposed to the first direction. The intervening section is disposed between the first and second sections. The first and second retainers face the first intervening section. The loop also has a second half having an elongate second half body having a third section, a fourth section and a second intervening section. A plurality of third retainers project peripherally from the third section along at least a portion thereof, in a second direction. A plurality of fourth retainers project peripherally from the fourth section along at least a portion thereof in a direction opposed to the second direction. The second intervening section is disposed between the third and fourth sections and the third and fourth retainers face the second intervening section.

The present invention still further provides for a continuous length of suture where the ends are joined together to form a loop. The loop has a plurality of sections of suture length. Each section has an elongate body having a first part, a second part and an intervening part located between the first part and the second part. A plurality of first retainers project from the first part in a first direction. The first retainers are disposed on the periphery of the body along at least a portion of the first part. A plurality of second retainers project from the second part in a second direction. The second direction being opposite to the first direction. The second retainers are disposed on the periphery of the body along at least a portion of the second part. Substantially all of the first retainers of the first part of each section and substantially all of the second retainers from the second part of each section face the intervening part of each section.

The present invention further provides for a method of supporting an object within the body of a mammal. The steps include providing a continuous length of suture where the ends of the suture are joined forming a loop, the loop having a first half and a second half. The first half of the loop has an elongate first half body having a first section, a second section and a first intervening section, a plurality of first retainers projecting peripherally from the first section along at least a portion thereof, in a first direction, a plurality of second retainers projecting peripherally from the second section along at least a portion thereof in a direction opposed to the first direction, and the intervening section disposed between the first and second sections where the first and second retainers face the intervening section. The loop also has a second half having an elongate second half body having a third section, a fourth section and a second intervening section, a plurality of third retainers projecting peripherally from the third section along at least a portion thereof, in a second direction, a plurality of fourth retainers projecting peripherally from the fourth section along at least a portion thereof in a direction opposed to the second direction, and the second intervening section disposed between the third and fourth sections where the third and fourth retainers face the second intervening section. The method further includes placing the point in the loop where the first and second halves are joined under an object within the body of a mammal to be supported. The method includes inserting the first half of the loop into a first section of tissue of a mammal at a point along the first intervening section forming a first insertion pathway, and inserting the second half of the loop into a second section of tissue forming a second insertion pathway, whereby the object within the body of a mammal is supported.

The present invention further provides for a method of supporting an object within the body of a mammal. The method includes the step of providing a continuous length of suture where the ends of the suture are joined forming a loop. The loop has a first length of suture having an elongate first body, a plurality of first retainers projecting from the first body in a first direction, the first retainers being disposed on the periphery of the first body along at least a portion of the first length. The loop also has a second length having a plurality of second retainers projecting from the second body in a second direction, the second direction being opposite to the first direction, the second retainers being disposed on the periphery of the second body along at least a portion of the second length. The loop has an intervening length located between the first and second lengths. Whereby substantially all of the first retainers and substantially all of the second retainers face the intervening length. The loop also has a diverging length where the first length and second lengths are joined and where the first retainers and second retainers diverge and face in opposing direction. The method also includes the steps of placing at least a portion of the diverging length under an object within the body of a mammal to be supported, and inserting the suture into a section of tissue of a mammal at a point along the intervening section forming an insertion pathway, whereby the object within the body of a mammal is supported.

The present invention also provides for a method of supporting an object within the body of a mammal by providing a continuous length of suture where the ends of the suture are joined forming a loop. The loop has a plurality of sections of suture length. Each section has an elongate body having a first part, a second part and an intervening part located between the first part and the second part. A plurality of first retainers project from the first part in a first direction, the first retainers being disposed on the periphery of the body along at least a portion of the first part. A plurality of second retainers project from the second part in a second direction, the second direction being opposite to the first direction, the second retainers being disposed on the periphery of the second body along at least a portion of the second length. The first retainers of the first part of each section and the second retainers from the second part of each section face the intervening part of each section. The method further includes the steps of placing a portion of the length of suture between sections under an object within the body of a mammal to be supported, inserting a first section of suture length into a first section of tissue of a mammal at a point along the first intervening part forming a first insertion pathway, and inserting the each remaining section of suture length into a subsequent section of tissue forming subsequent insertion pathways, whereby the object within the body of a mammal is supported.

The present invention yet further provides for a suture insertion device for use in inserting a length of suture into the tissue of a mammal. The suture insertion device has a substantially rigid, elongate body having a first end, a second end and a length. The suture insertion device also has a recess proximate to the first end to receive a cross-section of suture, and a forwardly extending finger located at the rearward end of the recess for maintaining the suture within the recess during insertion.

The present invention still further provides for an assembly for inserting a length of suture within the body of a mammal. The assembly has a length of suture having an elongated body having a first end, a second end, and a plurality of retainers projecting from the body. The retainers are disposed on the periphery of the body along at least a portion of the length of the body. The retainers face the first end, and are configured such that when the length of suture is inserted into the tissue of a mammal the retainers generally flex toward the body during insertion where damage to the tissue by the retainers is minimized, and the retainers are generally rigid and resist movement when the suture is pulled in a direction opposed to the insertion pathway. The length of suture also has a temporary holding point for receipt within a recess within a suture insertion device to hold the body. The temporary holding point is located proximate to the first end. The assembly also has a suture insertion device having a substantially rigid, elongate body having a first end, a second end and a length, a recess proximate to the first end to receive a cross-section of suture, and a forwardly extending finger located at the rearward end of the recess. When the temporary holding point is received within the recess of the suture insertion device, the length of suture is inserted within the body of a mammal via the suture insertion device in a first direction with the length of suture received within the recess, and the is withdrawn by moving the suture insertion device in a direction opposed to the first direction, the holding point being released from its position within the recess and thus frees the suture insertion device for removal therefrom.

The present invention further provides for another assembly for inserting a length of suture within the body of a mammal. The assembly includes a suture having an elongated body having a first end, a second end, and an intervening point located between the first and second ends. The suture also includes a plurality of retainers projecting from the body, the retainers being disposed on the periphery of the body along at least a portion of the length of the body, all of the retainers from both ends facing the intervening point. The retainers are configured such that when the length of suture is inserted into the tissue of a mammal at the intervening point, the retainers generally flex toward the body during insertion where damage to the tissue by the retainers is minimized, and the retainers are generally rigid and resist movement when the suture is pulled in a direction opposed to the insertion pathway. The assembly also includes a suture insertion device having a substantially rigid, elongate body having a first end, a second end and a length, a recess proximate to the first end to receive a cross-section of suture, and a forwardly extending finger located at the rearward end of the recess. When the intervening point is received within the recess of the suture insertion device, the length of suture is inserted within the body of a mammal by moving the suture insertion device in a first direction within the body of a mammal, when at least a portion of the length of suture is received within the body of the mammal, the suture insertion device is withdrawn from the body of a mammal by moving the suture insertion device in a direction opposed to the first direction, as a result of the opposed movement of the suture insertion device, the intervening point is released from its position within the recess and enables the suture insertion device to be withdrawn while allowing the length of suture to remain within the body of a mammal.

The present invention provides for a further assembly for inserting a length of suture within the body of a mammal. The assembly has a continuous length of suture and a suture insertion device. The continuous length of suture is joined at the ends to form a loop. The loop has a first length of suture having an elongate first body, a plurality of first retainers projecting from the first body in a first direction, the first retainers being disposed on the periphery of the first body along at least a portion of the first length. The loop has a second length having a plurality of second retainers projecting from the second body in a second direction, the second direction being opposite to the first direction, the second retainers being disposed on the periphery of the second body along at least a portion of the second length. The loop has an intervening length located between the first and second lengths, and substantially all of the first retainers and substantially all of the second retainers face the intervening length. The suture insertion device has a substantially rigid, elongate body having a first end, a second end and a length, a recess proximate to the first end to receive a cross-section of suture, and a forwardly extending finger located at the rearward end of the recess. When the intervening length is received within the recess of the suture insertion device, the length of suture is inserted within the body of a mammal by moving the suture insertion device in an insertion direction. When at least a portion of the length of suture is received within the body of the mammal, the suture insertion device is withdrawn from the body of a mammal by moving the suture insertion device in a direction opposed to the insertion direction, as a result of the opposed movement of the suture insertion device, the intervening length is released from its position within the recess and the suture insertion device is able to be withdrawn while enabling the length of suture to remain within the body of a mammal.

The present invention still further provides an assembly for inserting a length of suture within the body of a mammal. The assembly includes a continuous length of suture where the ends are joined together to form a loop, and a suture insertion device. The loop has a first half having an elongate first half body having a first section, a second section and a first intervening section. A plurality of first retainers project peripherally from the first section along at least a portion thereof, in a first direction. A plurality: of second retainers project peripherally from the second section along at least a portion thereof in a direction opposed to the first direction. The intervening section is disposed between the first and second sections where the first and second retainers face the first intervening section. The second half of the loop has an elongate second half body having a third section, a forth section and a second intervening section. A plurality of third retainers project peripherally from the third section along at least a portion thereof, in a second direction. A plurality of fourth retainers project peripherally from the fourth section along at least a portion thereof in a direction opposed to the second direction. The second intervening section is disposed between the third and fourth sections where the third and fourth retainers face the second intervening section. The suture insertion device has a substantially rigid, elongate body having a first end, a second end and a length, a recess proximate to the first end to receive a cross-section of suture, and a forwardly extending finger located at the rearward end of the recess. When the first intervening length is received within the recess of the suture insertion device, the first half is inserted within the body of a mammal by moving the suture insertion device in a first insertion direction. When at least a portion of the first half is received within the body of the mammal, the suture insertion device is withdrawn from the body of a mammal by moving the suture insertion device in a direction opposed to the first insertion direction. As a result of the opposed movement of the suture insertion device, the first intervening length is released from its position within the recess, and enables the suture insertion device to be withdrawn while enabling the first half to remain within the body of a mammal. When the second intervening length is received within the recess of the suture insertion device, the second half is inserted within the body of a mammal by moving the suture insertion device in a second insertion direction. When at least a portion of the second half is received within the body of the mammal, the suture insertion device is withdrawn from the body of a mammal by moving the suture insertion device in a direction opposed to the second insertion direction. As a result of the opposed movement of the suture insertion device, the second intervening length is released from its position within the recess and enables the suture insertion device to be withdrawn while enabling the second half to remain within the body of the mammal.

The present invention provides for another assembly for inserting a length of suture within the body of a mammal. The assembly includes a continuous length of suture where the ends are joined together to form a loop and a suture insertion device. The loop has a plurality of sections of suture length. Each section has an elongate body having a first part, a second part and an intervening part located between the first part and the second part. A plurality of first retainers project from the first part in a first direction. The first retainers are disposed on the periphery of the body along at least a portion of the first part. A plurality of second retainers project from the second part in a second direction, the second direction being opposite to the first direction. The second retainers are disposed on the periphery of the second body along at least a portion of the second length. Substantially of the first retainers of the first part of each section and substantially all of the second retainers from the second part of each section face the intervening part of each section. The suture insertion device has a substantially rigid, elongate body having a first end, a second end and a length, a recess proximate to the first end to receive a cross-section of suture, and a forwardly extending finger located at the rearward end of the recess. When each intervening part is separately, received within the recess of the suture insertion device, the corresponding section of suture is inserted within the body of a mammal by moving the suture insertion device in a first insertion direction. When at least a portion of that section of suture is received within the body of the mammal, the suture insertion device is withdrawn from the body of a mammal by moving the suture insertion device in a direction opposed to the first insertion direction, as a result of the opposed movement of the suture insertion device, the intervening part is released from its position within the recess and enables the suture insertion device to be withdrawn while enabling the section of suture inserted to remain within the body of the mammal. The insertion of remaining sections is similarly repeated until all sections of the length of suture are inserted into a body of a mammal.

The present invention further provides for a method of anchoring a suture within the body of a mammal. The method includes the steps of providing an assembly having a length of suture and a suture insertion device. The length of suture has an elongated body having a first end, a second end, and a plurality of retainers projecting from the body. The retainers are disposed on the periphery of the body along at least a portion of the length of the body. The retainers face the first end, and are configured such that when the length of suture is inserted into the body of a mammal the retainers generally flex toward the body during insertion where damage to the tissue by the retainers is minimized, and the retainers are generally rigid and resist movement when the suture is pulled in a direction opposed to the insertion pathway. The length of suture also has a temporary holding point to be received by a suture insertion device. The temporary holding point is located proximate to the first end. The suture insertion device has a substantially rigid, elongate body having a first end, a second end and a length, and a recess proximate to the first end to receive a length of suture. The method further includes placing a portion of the temporary holding point within the recess of the suture insertion device, inserting the suture insertion device, so as to form an insertion pathway, into the body of a mammal until the first end of the suture reaches a predetermined location, retrieving the suture insertion device in a direction substantially opposed to the insertion pathway until the suture insertion device is removed from the body of a mammal, and causing the length of suture to remain in the body of a mammal.

The present invention still further provides for a method of anchoring a suture within the body of a mammal. The method includes providing an assembly having a length of suture where the ends are joined together to form a loop. The loop has a first length of suture having an elongate first body, a plurality of first retainers projecting from the first body in a first direction, the first retainers being disposed on the periphery of the first body along at least a portion of the first length, a second length having a plurality of second retainers projecting from the second body in a second direction, the second direction being opposite to the first direction, the second retainers being disposed on the periphery of the second body along at least a portion of the second length, and an intervening length located between the first and second lengths, whereby all of the first retainers and all of the second retainers face the intervening length. The assembly further includes a suture insertion device having a substantially rigid, elongate body having a first end, a second end and a length, and a recess proximate to the first end to receive a length of suture. The method further includes placing a portion of the intervening length within the recess of the suture insertion device, inserting the suture insertion device into the body of a mammal so as to form a suture insertion device insertion pathway until the recess reaches a predetermined location, retrieving the suture insertion device substantially along the insertion pathway until the suture insertion device is removed from the body of a mammal, and causing the length of suture to remain in the body of a mammal.

The present invention further provides for a method of anchoring a suture within the body of a mammal. The method includes providing an assembly having a continuous length of suture where the ends are joined together to form a loop. The loop has a first half having an elongate first half body having a first section, a second section and a first intervening section, a plurality of first retainers projecting peripherally from the first section along at least a portion thereof, in a first direction, a plurality of second retainers projecting peripherally from the second section along at least a portion thereof in a direction opposed to the first direction, and the intervening section disposed between the first and second sections where the first and second retainers face the first intervening section; and a second half having an elongate second half body having a third section, a fourth section and a second intervening section, a plurality of third retainers projecting peripherally from the third section along at least a portion thereof, in a second direction, a plurality of fourth retainers projecting peripherally from the fourth section along at least a portion thereof in a direction opposed to the second direction, and the second intervening section disposed between the third and fourth sections where the third and fourth retainers face the second intervening section. The assembly also includes a suture insertion device having a substantially rigid, elongate body having a first end, a second end and a length, and a recess proximate to the first end to receive a length of suture. The method also includes placing a portion of the first intervening length of suture within the recess of the suture insertion device, inserting the suture insertion device into the body of a mammal until the recess reaches a predetermined location so as to form a first suture insertion device insertion pathway, retrieving the suture insertion device substantially along the insertion pathway until the suture insertion device is removed from the body of a mammal. The method further includes placing a portion of the second intervening length of suture within the recess of the suture insertion device, inserting the suture insertion device into the body of a mammal until the recess reaches a predetermined location so as to form a second suture insertion device insertion pathway, retrieving the suture insertion device substantially along the second insertion pathway until the suture insertion device is removed from the body of a mammal, and causing the length of suture to remain in the body of a mammal.

The present invention still further provides for a method of anchoring a suture within the body of a mammal. The method includes the steps of providing an assembly having a continuous length of suture where the ends are joined together to form a loop, and a suture insertion device. The loop has a plurality of sections of suture length, each section having an elongate body having a first part, a second part and an intervening part located between the first part and the second part, a plurality of first retainers projecting from the first part in a first direction, the first retainers being disposed on the periphery of the body along at least a portion of the first part, and a plurality of second retainers projecting from the second part in a second direction, the second direction being opposite to the first direction, the second retainers being disposed on the periphery of the second body along at least a portion of the second length, all of the first retainers of the first part of each section and all of the second retainers from the second part of each section face the intervening part of each section. The suture insertion device has a substantially rigid, elongate body having a first end, a second end and a length, and a recess proximate to the first end to receive a length of suture. The method further includes placing a portion of the intervening part within the recess of the suture insertion device, inserting the suture insertion device into the body of a mammal so as to form a suture insertion device insertion pathway until the recess reaches a predetermined location, retrieving the suture insertion device substantially along the insertion pathway until the suture insertion device is removed from the body of a mammal causing the length of suture to remain in the body of a mammal, and repeating the inserting and retrieving steps until all sections of the loop are inserted into the body of a mammal.

The present invention also provides for a self-retaining suture having an elongated body having a first end, a second end and a first section and a second section, a plurality of retainers projecting from the body along the first section in a first direction, and a plurality of retainers projecting from the body along the second section in a second direction. The first direction is opposed to the second direction. The retainers of the first section face the retainers of the second section, and the retainers being configured such that when the length of suture is inserted into the tissue of a mammal at the point where the retainers converge, the retainers generally flex toward the body during insertion where damage to the tissue by the retainers is minimized, and the retainers generally resist movement when the suture is pulled in a direction opposed to the insertion pathway.

The present invention yet further provides for a method of using a self-retaining suture comprising the steps of providing a self-retaining suture having an elongated body having a first end, a second end and a first section and a second section, a plurality of retainers projecting from the body along the first section in a first direction, and a plurality of retainers projecting from the body along the second section in a second direction, the first direction being opposed to the second direction. The method also includes providing a suture insertion device having a substantially rigid, elongate body having a first device end, a second device end and a device length, and a recess proximate to the first device end to receive a cross section of suture. The method further includes placing a cross-section of the self-retaining suture into the recess of the suture insertion device at a place along the length of the suture between the first and second sections, and inserting the first device end into the body of a mammal so as to from an insertion pathway until the recess reaches a predetermined location. The method further includes retrieving the suture insertion device by substantially reversing direction along the insertion pathway until the suture insertion device is removed from the body of a mammal, and causing the suture to remain in the body of a mammal, whereby when the suture is inserted into the tissue of a mammal, the retainers generally flex toward the body during insertion where damage to the tissue by the retainers is minimized, and the retainers generally resist movement when the suture is pulled in a direction opposed to the insertion pathway.

The details of one or more aspects or embodiments are set forth in the description below. Other features, objects and advantages will be apparent from the description, the drawings, and the claims. In addition, the disclosures of all patents and patent applications referenced herein are incorporated by reference in their entirety.

DESCRIPTION OF INVENTION

Figure 1:
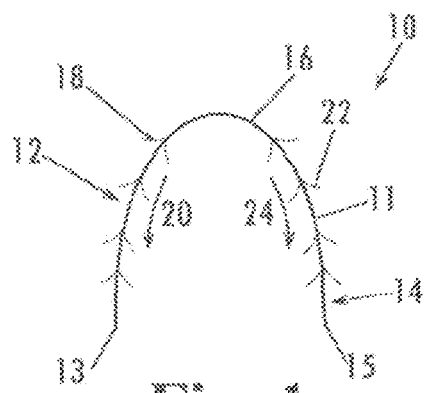
FIG. 1 is a front view of a first embodiment of the present invention.

Certain terminology is used herein for convenience only and is not to be taken as a limitation on the invention. For example, words such as "first" and "second", "forward" and "rearward", "inner" and "outer" merely describe the configuration shown in the figures. Indeed, the referenced components may be oriented in any direction and the terminology, therefore, should be understood as encompassing such variations unless specified otherwise.

In addition, prior to setting forth the invention, it may be helpful to an understanding thereof to first set forth definitions of certain terms that are used hereinafter.

"Self-retaining system" refers to a self-retaining suture together with means for deploying the suture into tissue. Such deployment means include, without limitation, suture needles and deployment devices as well as sufficiently rigid and sharp portions on the suture itself to penetrate tissue.

"Self-retaining suture" refers to a suture that does not require a knot or a suture anchor in order to maintain its position into which it is deployed during a surgical procedure. These may be monofilament sutures or braided sutures, and are positioned in tissue in two stages, namely deployment and affixation, and include at least one tissue retainer.

"Tissue retainer" (or simply "retainer") or "barb" refers to a suture element having a retainer body projecting from the suture body and a retainer end adapted to penetrate tissue. Each retainer is adapted to resist movement of the suture in a direction other than the direction in which the suture is deployed into the tissue by the surgeon, by being oriented to substantially face the deployment direction. As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from their deployment positions (i.e., resting substantially along the suture body), forces the retainer ends to open from the suture body in a manner that catches and penetrates into the surrounding tissue, and results in tissue being caught between the retainer and the suture body; thereby "anchoring" or affixing the self retaining suture in place.

"Retainer configurations" refers to configurations of tissue retainers and can include features such as size, shape, surface characteristics, and so forth. These are sometimes also referred to as "barb configurations".

"Suture thread" refers to the filamentary body component of the suture, and, for sutures requiring needle deployment, does not include the suture needle. The suture thread may be monofilamentary, or, multifilamentary.

"Monofilament suture" or "monofilament" refers to a suture comprising a monofilamentary suture thread.

"Braided suture" refers to a suture comprising a multifilamentary suture thread. The filaments in such suture threads are typically braided, twisted, or woven together.

"Degradable (also referred to as "biodegradable" or "bioabsorbable") suture" refers to a suture which, after introduction into a tissue is broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination or these) or by a thermal or photolytic process. Polymer degradation may be characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). These sutures can be in either a braided multifilament form or a monofilament form. The polymers used in the present invention can be linear polymers, branched polymers or multi-axial polymers. Examples of multi-axial polymers used in sutures are described in U.S. Patent Application Publication Nos. 2002/161168, now abandoned, 2004/0024169, issued as U.S. Pat. No. 7,026,437 on Apr. 11, 2006, and 2004/0116620, issued as U.S. Pat. No. 7,070,858 on Jul. 4, 2006. Sutures made from degradable suture material lose tensile strength as the material degrades.

"Non-degradable (also referred to as "non-absorbable") suture" refers to a suture comprising material that is not degraded by chain scission such as chemical reaction processes (e.g., hydrolysis, oxidation/reduction, enzymatic mechanisms or a combination or these) or by a thermal or photolytic process. Non-degradable suture material includes polyamide (also known as nylon, such as nylon 6 and nylon 6.6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Needle attachment" refers to the attachment of a needle to a suture requiring same for deployment into tissue, and can include methods such as crimping, swaging, using adhesives, and so forth. The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging whereby the suture material is inserted into a channel at the blunt end of the needle which is then deformed to a final shape to hold the suture and needle together. In the traumatic needle the thread comes out of the needle's hole on both sides and often the suture rips the tissues to a certain extent as it passes through. Most modern sutures are swaged atraumatic needles. Atraumatic needles may be permanently swaged to the suture, or may be designed to conic off the suture with a sharp straight tug. These "pop-offs" are commonly used for interrupted sutures, where each suture is only passed once and then tied.

Suture needles may also be classified according to their point geometry. For example, needles may be (i) "tapered" whereby the needle body is round and tapers smoothly to a point; (ii) "cutting" whereby the needle body is triangular and has sharpened cutting edge on the inside; (iii) "reverse cutting" whereby the cutting edge is on the outside; (iv) "trocar point" or "tapercut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030 (Mani, Inc., Japan); and U.S. Pat. No. 5,464,422 (W.L. Gore, Newark, Del.); and U.S. Pat. Nos. 5,941,899; 5,425,746; 5,306,288 and 5,156,615 (US Surgical Corp., Norwalk, Conn.); and U.S. Pat. No. 5,312,422 (Linvatec Corp., Largo, Fla.); and U.S. Pat. No. 7,063,716 (Tyco Healthcare, North Haven, Conn.). Other suturing needles are described, for example, in U.S. Pat. Nos. 6,129,741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth).

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a gunshot, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

"Tissue elevation procedure" refers to a surgical procedure for repositioning tissue from a lower elevation to a higher elevation (i.e., moving the tissue in a direction opposite to the direction of gravity), The retaining ligaments of the face support facial soft tissue in the normal anatomic position. However, with age, gravitational effects achieve a downward pull on this tissue and the underlying ligaments, and fat descends into the plane between the superficial and deep facial fascia, thus allowing facial tissue to sag. Face-lift procedures are designed to lift these sagging tissues, and are one example of a more general class of medical procedure known as a tissue elevation procedure. More generally, a tissue elevation procedure reverses the appearance change that results from gravitation effects over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Medical device" or "implant" refers to any object placed in the body for the purpose of restoring physiological function, reducing/alleviating symptoms associated with disease, and/or repairing/replacing damaged or diseased organs and tissues. While normally composed of biologically compatible synthetic materials (e.g., medical-grade stainless steel, titanium and other metals: polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopaedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

As discussed above, the present invention provides compositions, configurations, methods of manufacturing and methods of using self-retaining systems in surgical procedures which greatly increase their ability to anchor into the surrounding tissue to provide superior holding strength and improve clinical performance.

Referring now to the drawings, wherein like reference numerals designate corresponding or similar elements throughout the several views, FIG. 1 shows a front view of the first embodiment of the present invention. The first embodiment of the present invention includes a length of suture 10 and having a first section 12, a second section 14 and an intervening section 16. The length of suture 10 has an elongated body 11 and free ends 13 and 15. The first section 12 has free end 13 and a plurality of first retainers 18 extending from the periphery of the length of the first section in a first direction, indicated by arrow 20. The arrow 20 indicates the direction in which the suture is pulled to cause the retainers to flex outwardly The second section 14 has free end 15 and a plurality of second retainers 22 extending from the periphery of the length of the second section in a second direction, indicated by arrow 21. The second direction is opposed to the first direction. Both the first retainers 18 and the second retainers 22 face the intervening section 16 and thus each other. The intervening section 16 has no retainers thereon.

Figure 2A:
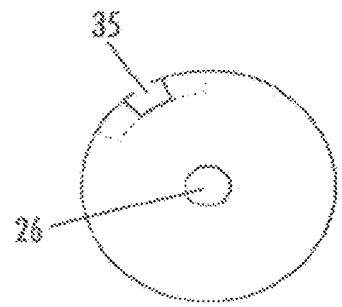
FIG. 2A is a front view of a suture insertion device of the present invention.
Figure 2B:
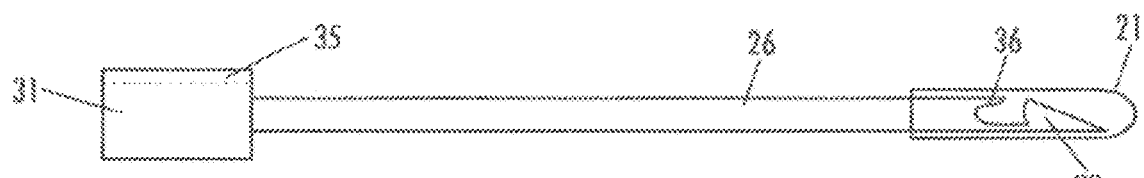
FIG. 2B is a side view of the embodiment of FIG. 2A.
Figure 3:
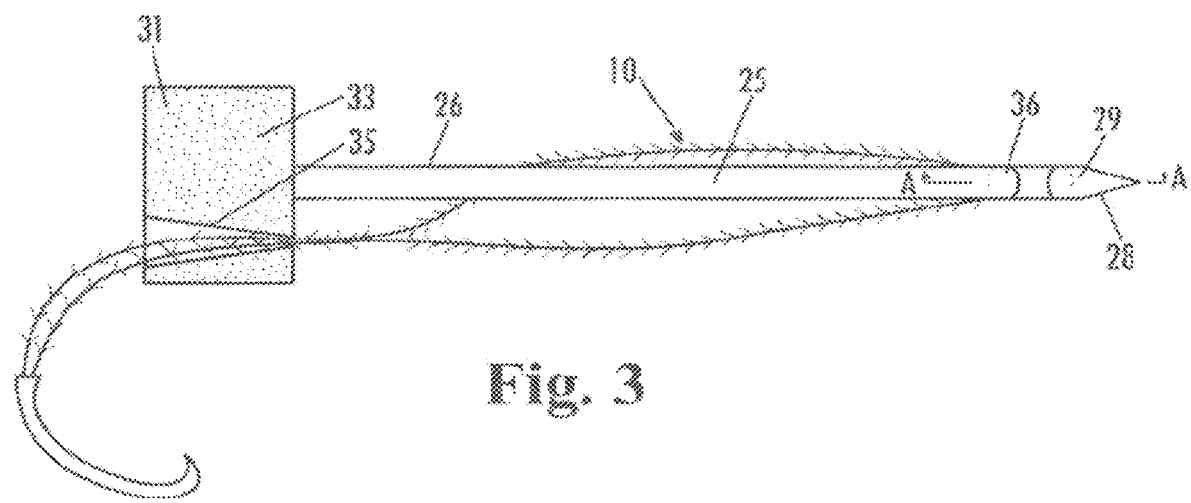
FIG. 3 is a top view of the suture insertion device of FIG. 2A with the first embodiment of FIG. 1 held therein.

FIGS. 2A and 2B show a suture insertion device 26 of the present invention. FIG. 3 shows the suture insertion device assembled with a length of self-retaining suture 10 of the embodiment shown in FIG. 1. As shown in FIGS. 2A and 2B, the device 26 includes a relatively straight needle body 25 having a pointed first device end 28, a second device end 30 and a length 32. A protective cover 21 covers the pointed end 28 to prevent needle sticks. A recess 34 is located proximate to the first device end 28. The recess 34 is for receiving a cross-sectional portion of the intervening section 16. Thus the recess 34 must be sized appropriately to accommodate the diameter of the suture 10. It should also be noted that the intervening section 16 must be of sufficient length so as to enable the intervening length to properly rest within the recess 34 without the first 12 or second sections 14 of retainers extending therein. The first suture insertion device end 28 also includes a forwardly facing finger 36. The finger 36 serves to hold the cross-section of the intervening section 16 during insertion into a body of a mammal, as discussed in more detail below. The length and diameter of the finger 36 will vary depending upon the suture insertion device 26 size and the suture 10 diameter. The device 26 also includes a rearwardly extending member 29 adjacent to the first device end 28. The rearwardly extending member 29 also serves to hold the suture within the recess during forward movement of the device 26. The length of the suture insertion device 26 opposed to the recess 36, is the underside 38. The underside 38 of the suture insertion device is sharpened so that it may easily cut an insertion pathway as the suture insertion device 26 is inserted into the body of a mammal, as will be discussed in more detail below. A handle 31 is located proximate and fixed to the second device end 30. The handle 31 serves as a holding point for the user during use. The handle 31 includes a handle body 33 having a length and a suture holding channel 35 extending along the side of the handle along its length. The suture holding channel 35 is sized to receive a length of suture of the present invention during use, which will be discussed in detail below.

Figure 4:
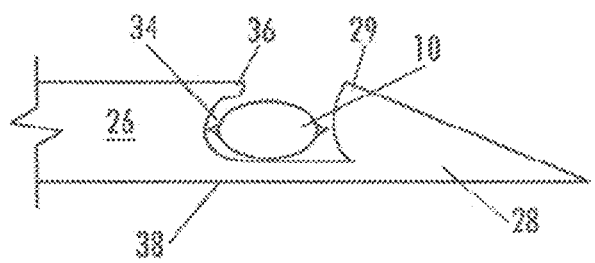
FIG. 4 is an enlarged sectional view of a portion of the assembly of FIG. 3 taken along line A-A.

In use, the assembly of the suture length 10 and suture insertion device 26 are designed to be inserted into the body of a mammal. This procedure may be for the purpose of binding a wound, closing an incision or endoscopic port. Such that, when the length of suture is received within the recess 34 the intervening section 16 is relatively perpendicular to the suture insertion device length 32 at that point, as shown in FIG. 3. FIG. 4 also shows an enlarged view of the cross-section of the intervening section 16 of the length of suture 10 received into the recess 34 of the suture insertion device 26. After the protective cover 21 is removed from the first end 28 of the suture insertion device 26, it is then inserted into a section of the body of the mammal, typically within a section of tissue that will provide support for the first 18 and second retainers 22 upon removal of the suture insertion device, such as a section of muscle. As the suture insertion device 26 moves in a forwardly direction, the device holds the length of suture 10 within its recess 34. The finger 36 helps to hold the intervening section 16 within the recess 34 during forward travel of the device 26. The sharpened underside 28 of the device 26 cuts through the mammalian tissue to form an insertion pathway 40. In addition, as the length of suture 10 moves in a forwardly direction, the first 18 and second 22 retainers flex and remain close to the perimeter of the suture body 11. When the first 12 and second 14 sections of the suture length 10 have been completely inserted into the body of a mammal, the user stops the forward travel of the device 26. The user then begins to remove the device 26 by moving the device in a direction substantially opposed to the insertion pathway. As this occurs, the opposed movement of the device 26 enables the intervening section 16 to free itself from its location within the recess 34. The finger 36 no longer is able to hold the intervening section 16 within the recess 34 when the device 26 travels in an opposite direction from the insertion pathway. As a result, the intervening section 16 is freed from its position within the recess 34, and the device 26 may be completely removed from the tissue of the mammal by reversing the direction taken on the insertion pathway. At this time any movement of the suture length 10 in a direction opposed to the insertion pathway would result in the first 18 and second 22 retainers becoming rigid and opposing movement in a direction opposed to the insertion pathway by extending outwardly relative to the periphery of the suture body 11 and into the surrounding body of the mammal to secure the position of the first 12 or second 14 section at that location.

In the situation where a wound is being repaired or an incision is being closed, this method would further involve joining the length of suture with a second length of suture similarly inserted into the body of a mammal at an alternative location. The free ends of each length of suture would then be tied or joined in an appropriate fashion to complete the closure of the wound or incision.

In the case where the length of suture is inserted for the purpose of supporting a body part, such as a bladder neck, and other pelvic floor prolapsed conditions, the length of suture would be joined to at least one other length of suture similarly inserted into the body where the five ends would remain proximate to the body part to be supported. The part would be supported by joining the free ends of the lengths of suture 10 under the body part so as to form a sling or similar support member to ensure that the lengths of suture will prevent the body part from any further movement. Such ends may also be joined to a single piece of mesh or other material conductive to prolonged contact with the particular body part being suspended.

It is further anticipated that the free ends of the suture may be joined with a drug delivery agent, such as a chemotherapeutic agent for the precise localized delivery of chemotherapeutic drug to cancerous tissues such as in the prostrate and in tumor growths in other various locations. It is also anticipated that the suture may be attached to a tacking device for use in connection with mesh that is used in hernia repair. The tacks are used to hold the mesh in repairing herniated tissue while providing a profile that is less palpable to the patient. It is further anticipated that the suture may be attached to a marker for use in radiation therapy. It is anticipated that the suture may also be attached to a radio labeled tag for the identification of tissue in x-rays.

It should be stressed that the advantage of the present invention over the prior art provides a greater level of accuracy in fixing these items, such as markers, tags, tacks or therapeutic and drug delivery agents or the like to the self-retaining suture because the exact location of the item can be achieved by the needle or suture insertion device. With these items fixed to the suture, the surgeon or other medical professional can place the item in the precise location needed in the patient's body to provide maximum efficacy and can retrieve the needle or insertion device with no movement by the suture or the attachment because of the retainered configuration.

Figure 1A:
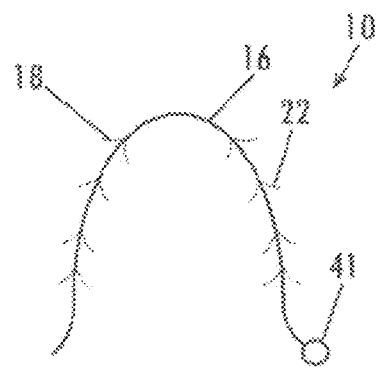
FIG. 1A is a front view of a first alternative embodiment of the embodiment of FIG.

It is anticipated that the free ends of the length of suture 10 may include an attachment loop 41 or other attachment means for fixing an object to the suture, as shown in FIG. 1A. This may be done ahead of time to securely fix an object, such as a tack, marker, therapeutic or chemotherapeutic agent to the suture length for insertion into a patient rather than making the attachment at the time of the procedure. This attachment ahead of time results in a more secure attachment and thus a more accurate placement since it is less likely that the object attached will move or the attachment means will fail.

In addition, because the attached items are inserted into the body by means of a suture that is inserted to the desired location and then reversed, the insertion device or needle does not create a further pathway through the tissue. This results in further assuring that the suture remains in its intended location because there is no further pathway for the suture to migrate. In some cases, standard suture may migrate along an insertion pathway if that pathway is cut or ripped or otherwise disrupted. In the present case, because the sutures are retainered and the suture and attachment are inserted using a detachable needle or insertion device, no further insertion pathway is created. Thus, potential migration of the suture and attachment are significantly prevented.

Also, because the insertion occurs only to the point of placement, neighboring tissue located beyond the placement point, is not disrupted and thus, damage to the surrounding tissue area is prevented. This results in minimal pain and exposure to infection for the patient. This also results in a higher success rate as complications resulting from surrounding tissue damage are eliminated.

In cases of chemotherapy delivered locally, it is critical to the success of the delivery of the chemotherapeutic drug that the drug delivery agent be located as close as possible to or at a specific site within the tumor being treated. With this assembly, the surgeon can deliver with fine accuracy the agent or item to the desired location and a reduced risk to adjacent normal tissue. This enables the drug agent to work at its maximum potential without loss of efficacy due to migration of the drug agent. Furthermore, in situations where markers are used for radiation therapy or the like, the greater the accuracy and localized placement of the marker, the more focused the radiation therapy on a particular location will be. In cases of using the suture assembly of the present invention with tacks in hernia repair, the repair procedure will have a higher success rate, if the tacks are anchored in such a way as to reduce migration. The present invention will provide sufficient reduction in migration as well as accurate placement of the tacks for such a procedure. Further, the present invention minimizes the profile of the tack overall, a favorable improvement over current larger tacking devices that are often palpable to the patient and thus a cause of patient distress.

It should be further noted that the attachments to the suture discussed above are equally applicable to the remaining embodiments that will be discussed in more detail below. In some cases, an alternative embodiment may provide greater attachment capability than the first embodiment discussed above. For instance, the embodiments having a continuous loop of suture may be more appropriately suited to the affixation of a marker or therapeutic agent than the single length which requires manual attachment.

Testing of First Embodiment of the Present Invention

Applicants have conducted tests relating to the self-retaining suture assembly described above. The tests were designed to determine the pull strength required to remove the self-retaining suture length of the first embodiment of the present invention from within a test sample of mammalian tissue. A total of 62 threads were tested. Some of the suture lengths were swedged onto a standard surgical needle. The standard surgical needle had a diameter of 0.68 mm. Other suture lengths were placed within the recess of the suture insertion device of the present invention as shown in FIGS. 2A and 2B. The diameter of the needle of the present invention was 0.70 mm. Another variable in the suture insertion device design was the curvature. Some of the samples tested had the suture length inserted by means of an attached needle and some of the samples tested had the suture length inserted by means of a detachable suture insertion device.

The term "attached" means that the needle was physically tied to the suture and detachment from the suture was accomplished by cutting the suture away from the needle. The term "detachable" means that the suture insertion device was designed in accordance with the embodiment discussed above. Each detachable suture insertion device had a recess for receiving a portion of the intervening length of the suture.

Some of the attached needles and some of the detachable suture insertion devices were straight and some of the attached needles and detachable suture insertion devices were curved. The attached needles were 0.70 mm in diameter and the detachable suture insertion devices had a diameter of 0.68 mm. It should be noted that the attached needle diameter cannot be made any smaller due to the present state of manufacture. The attached needle diameter must be of a minimum diameter to provide for the boring of its end to a sufficient clearance to receive the thread while retaining enough unbored perimeter to enable the perimeter to be swedged or crimped onto the suture body. At present, if the suture insertion device diameter is less than 0.70 mm, it will not provide a sufficient bore to allow the insertion of the diameter of the thread that was tested. This presents a further advantage of the present invention. Detached suture insertion devices of the present invention may be made smaller in diameter than currently available attached needles. This results in a less invasive procedure and may enable the self-retaining suture to grip the surrounding tissue more effectively since a narrower insertion pathway permits the retainers to make contact with the surrounding tissue with less flexure of the retainer. It should be further noted that a smaller diameter suture insertion device enables the use of a smaller diameter suture. These relative dimensions have been previously optimized in the cited prior art of Table 1.

The curved needles and suture insertion devices tested had a radius of curvature of 180°, 130 mm. The lengths of the attached needles and detached suture insertion devices were 50 mm. Both the attached straight and curved needles were made of surgical grade stainless steel and were made by B.G. Sulzle, Inc of Syracuse, N.Y. The detachable curved and straight suture insertion devices were made of stainless steel and were made by Prym-Dritz Corporation of Spartenburg, S.C.

The suture material was USP #1 black monofilament nylon supplied by Ashaway having a diameter of 0.433 mm. The suture length was 38 cm. The retainer dimensions were 1.0 mm in length, 0.16 mm in depth and the angle from the longitudinal axis was 27°. In addition, the retainers were arrayed in a helical pattern with one retainer being located every 1 mm. The retainer pattern completed 360° of rotation around the circumference of the suture for each 8 mm of suture length.

Figure 5:
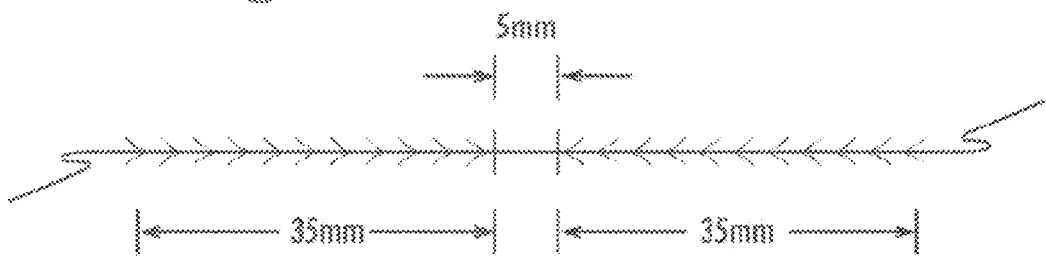
FIG. 5 is a diagrammatic representation of the tested suture length having converging retainers thereon.

In addition, there were three types of suture arrangements used in the testing. The first group was standard suture having no retainers at all. This group is described as "0×0". The second group had retainers on one side of the suture only (referred to as "1×0"). The third group had retainers on both sides of the suture length (referred to as "1×1"). In the second and third groups, a single section of retainers had a length of 3.5 cm. In the case of the third group, the space between facing retainers was 5 mm. A diagram of the retainer configuration for the third group is shown in FIG. 5.

The test samples were pork shoulder segments cut into rectangular strips having the following dimensions: 3 cm wide, 10 cm long and 4 cm thick. The tissue had no skin and consisted essentially of muscle with varying amounts of fat and fascia. This tissue is considered to be similar in structure/performance to that of soft tissue located in the pelvic floor and in other areas of the human body, such as where access ports are made for endoscopic procedures. Each tissue sample was marked using a guide to ensure that the self-retaining suture lengths would be fully inserted in each sample tested. The markings indicated where the self-retaining suture lengths started and ended. The markings were located in substantially the lower half of the longitudinal axis of the each sample. This was done to ensure that each sample had sufficient length on the upper portion to enable an effective grip by the tensiometer without interfering with the suture length. The suture lengths were inserted into the tissue samples in one of two ways. For those inserted with a straight suture insertion device, the sutures were inserted with the suture insertion device at approximately the center point at one end and moved along the longitudinal axis of the tissue sample until all of the retainered section of the suture length was between the marking. For those test samples having an attached suture insertion device, the suture insertion device was moved through the tissue sample length along the longitudinal axis. Once the retainered sections were located between the markings, the suture insertion device was moved out of the tissue and severed from the suture.

For the tissue samples using a curved suture insertion device, the suture insertion device was inserted through a side of the tissue sample and moved along a curved insertion pathway. The curved insertion pathway samples were located approximately one-third of the length of the sample. Further, the samples that were threaded with needles having the suture attached thereto were moved through the insertion pathway. Once the full length of the self-retaining suture segment was contained within the tissue, the needle was guided outward from the tissue. Once the needle was cleared from the tissue, the suture was cut from the needle prior to testing.

The pull tests were performed by a Test Resources Universal Tester Tensiometer, model 200Q. The free ends of the suture length were attached between two sides of the bottom vice grip. The top of the tissue strip was attached between two sides of the top vice grip which had serrated surfaces on each side to achieve greater gripping strength on the sample. Care was taken to ensure that the portion of the tissue containing the suture was not held within the top vice grip. The tensiometer was operated at a rate of 10 inches per minute until either the suture broke or until the suture was pulled from the tissue sample. The tensiometer displayed the maximum pull-out force at the time of failure or pull out. A total of 62 threads were tested including those inserted by attached needles and detachable suture insertion devices, with one exception. The detachable suture insertion devices were the only type able to deliver the self-retaining suture segments having retainered portions on both sides of the length (e.g. the 1×1 segments). Of the 62 threads tested, 56 samples resulted in the sutures being pulled from the tissue, 4 samples resulted in thread breakage, and 2 resulted in the tissue segment pulling away from the top vice grip of the tensiometer prior to suture pull out or breakage. The maximum pull strength recorded for each sample, in ounces, is set forth below in Table 2

| | | | Data In Ounces | | | | | | | |
|---|---|---|---|---|---|---|---|---|---|---|
| Type | Needle Type | Pattern | 1 | 2 | 3 | 4 | 5 | 6 | 7 | Average |
| 0x0 | attached | Straight | 0.5 | 0.6 | 0.6 | 0.8 | 0.5 | n/a | n/a | 0.6 |
| 0x0 | detached | Straight | 2.4 | 2.2 | 1.9 | 2.2 | 2.2 | n/a | n/a | 2.2 |
| 0x0 | attached | Curved | 0.6 | 0.8 | 0.6 | 0.6 | 0.6 | n/a | n/a | 0.7 |
| 0x0 | detached | Curved | 2.7 | 2.6 | 5.4 | 2.6 | 2.1 | n/a | n/a | 3.1 |
| 1x0 | attached | Straight | 17.3 | 37.0 | 30.6 | 23.8 | 17.0 (B) | 43.4 | 49.9 | 31.3 |
| 1x0 | detached | Straight | 33.9 | 56.3 | 34.7 | 37.9 | 25.3 | 32.3 | 33.1 | 36.2 |
| 1x1 | detached | Straight | 43.2 | 31.2 | 35.8 | 25.3 | 52.8 | 29.9 | 26.7 | 35.0 |
| 1x0 | attached | Curved | 39.7 (B) | 31.0 (B) | 46.4 | 53.0 | 37.4 (B) | 42.7 | 43.5 | 42.0 |
| 1x0 | detached | Curved | 26.6 | 39.4 | 32.8 | 41.0 | 48.8 | 45.8 | 35.4 | 38.5 |
| 1x1 | detached | Curved | 43.4 | 67.4 | 66.6 | 55.0 | 65.4 (T) | 34.2 | 67.7 (T) | 57.1 |

Notes:
(B) Thread Broke
(T) Tissue separated from tensionmeter clasp

Figure 17:
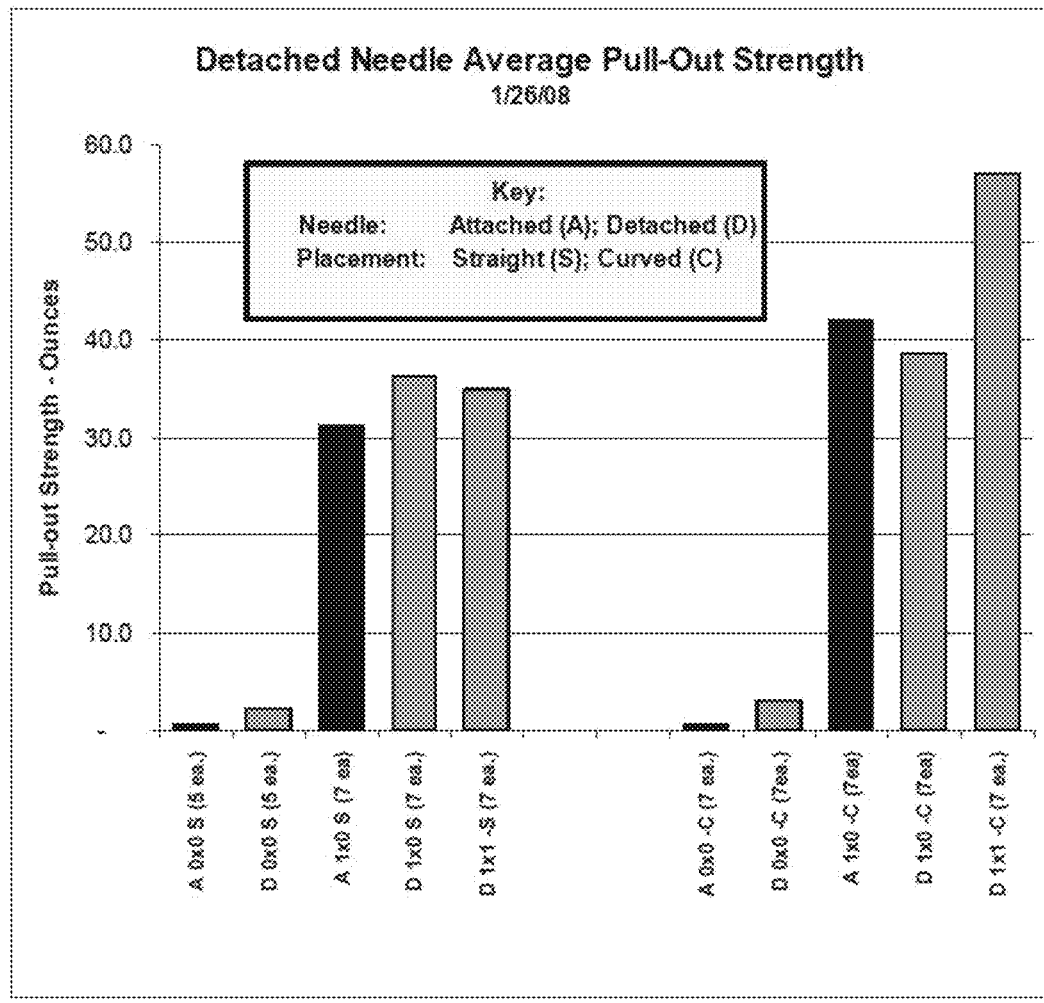
FIG. 17 is a table that provides a comparative; analysis regarding the pullout strength in ounces of various sutures tested.

FIG. 17 is a table that provides a comparative analysis regarding the pullout strength in ounces of each suture tested. The sutures are grouped into sample groups. The table indicates the average pull out strength of sutures with straight vs. curved insertion pathways, as well as those with attached needles and those using the suture insertion device of the present invention. Further, the table assesses the average pull strength of the different sutures having none, one or two sections with retainers thereon. As can be seen from the data in Table 3, the sutures having a curved pathway with both sections of the suture length having retainers thereon and having been inserted with the suture insertion device of the present invention, demonstrated the highest level of pull out strength. All test groups inserted with the suture insertion device of the present invention demonstrated at least equivalent holding strength when compared with sutures with similar retainer patterns that were delivered with an attached needle.

Alternative Embodiments of the Present Invention

Figure 6:
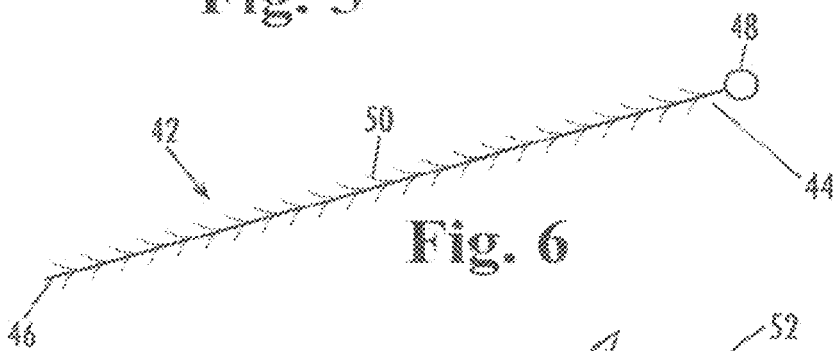
FIG. 6 is a front view of a second alternative embodiment of the present invention.

FIG. 6 shows a first alternative embodiment to the present invention of FIG. 1. FIG. 6 includes a length of suture 42 having a first end 44 and a second end 46. A loop 48 is located at the first end 44 of the length 42. A plurality of retainers 50 extend along the periphery of the length of suture 42. All of the retainers 50 face the loop 48. The loop 48 is relatively small relative to the length of suture 42.

In use, the cross-section of the loop 48 is received into the recess 34 of the suture insertion device 26 discussed in detail above. The suture insertion device 26 is inserted into a section of a body of a mammal. As discussed previously, it is preferable to insert the suture insertion device 26 with the suture 42 into a section of muscle so that the retainers 50 are better able to grab the muscle tissue and hold the suture 42 in place. Conversely, the insertion of the suture into an area of fat will not enable the retainers to effectively bind themselves to the surrounding fat and thus not enable the suture to be effective in its ability to bind a wound or support an organ or the like. Once the suture insertion device 26 is inserted into the tissue of a mammal, the finger 36 of the device holds the loop 48 within the recess 34 during forward travel of the device within the body. When the length of suture desired is fully inserted within the body of a mammal, the user stops the forward travel of the suture insertion device 26. The user removes the device 26 from the body by reversing the forward travel of the device. This results in a release of the loop 48 from its position within the recess 34 and enables the device to be completely removed from the body while enabling the length of suture 42 to remain in position within the body. During insertion of the suture length, the retainers 50 of the suture 42 flex towards the suture length. Conversely, if the length of suture 42 were pulled in a direction opposed to the insertion direction, the retainers 50 would become rigid and flex outwardly and resist movement in the opposed direction.

Figure 7:
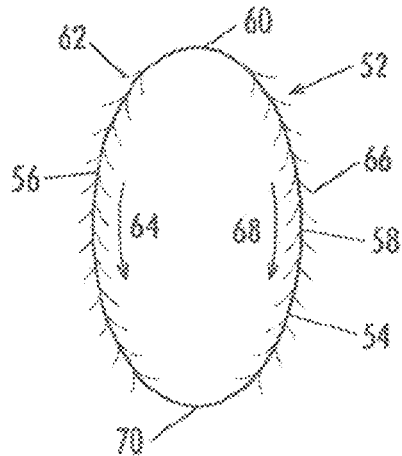
FIG. 7 is a front view of a third alternative embodiment of the present invention.

FIG. 7 of the present invention displays a further alternative to the present invention. This alternative includes a length of suture where the ends have been joined to form a second alternative looped suture 52. The loop 52 has an elongated second alternative length 54 that is generally circular in cross section. The loop 52 includes a first half 56 and a second half 58 and a second alternative intervening section 60. The intervening section 60 is located between the first 56 and second 58 halves. The first half 56 has a plurality of first half retainers 62 extending from the periphery of the length of the first half in a first direction, indicated by the arrow 64. Similarly, the second half 58 has a plurality of second half retainers 66 extending from the periphery of the length of the second half in a second direction, indicated by the arrow 68. The second direction is opposed to the first direction. Both the first half retainers 62 and the second half retainers 66 face the second alternative intervening section 60 and thus each other. In the present embodiment, there also exists empty loop space 70 located at the divergence of the first half retainers 62 and second half retainers 66. The empty loop space 70 may be used as a support for an organ or other body part when in use.

Figure 7A:
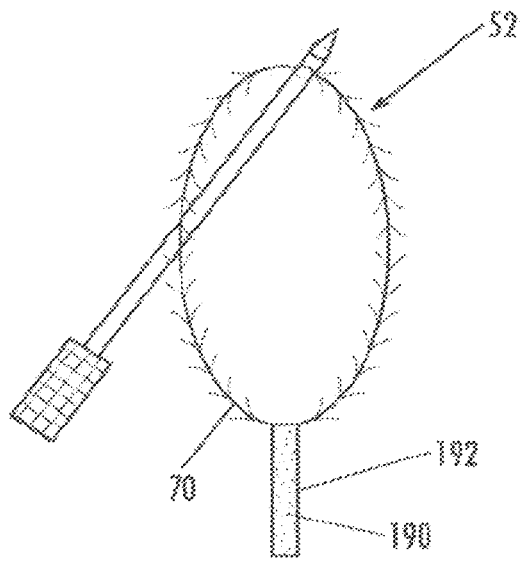
FIG. 7A is a perspective view of the embodiment of FIG. 7 having an object attached thereto.
Figure 7B:
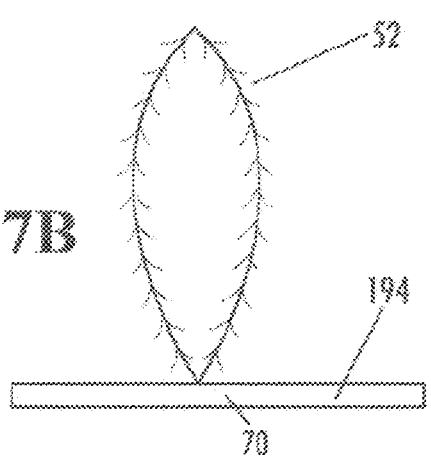
FIG. 7B is a front view of the embodiment of FIG. 7 having a tack attached thereto.

In use, the assembly of the looped suture 52 and suture insertion device 26 are designed to be inserted into the body of a mammal. This procedure may be for the purpose of binding a wound, closing an incision or attaching an object such as a surgical tack, implant, marker or chemotherapeutic agent. FIGS. 7A and 7B show proposed uses of the embodiment shown in FIG. 7. Because the present invention provides for the effective and accurate anchoring of a length of suture within mammalian tissue, it is anticipated that such self-retaining suture lengths or loops may be used to fix objects within tissue as well. As discussed above with respect to previous embodiments, the self-retaining suture embodiment of FIG. 7 may be used to effectively fix a chemotherapeutic agent into the body of a mammal, as shown in FIG. 7A. The chemotherapeutic agent 190 is embedded within a polymer resin structure 192 and attached to the empty loop space 70 of the second alternative looped structure 52. The chemotherapeutic agent 190 is designed to be controllably released into the mammal's body at a specific rate.

FIG. 7B shows the second alternative looped structure 52 of FIG. 7 with a surgical tack 194 attached to the empty loop space 70. The tacks are used primarily in hernia procedures as discussed in detail above. The looped configuration of the second alternative looped structure 52 may be more suited to attachment of objects as the loop is a closed structure and there is less opportunity for the object to disconnect or break away from the loop structure than a length of suture with an object manually attached as described above. It should be noted that the embodiments of FIGS. 7A and 79 could also be used with a single length of suture 42 as shown in FIG. 6, or with a length of converging retainers as shown in FIG. 1A and discussed in detail above.

Figure 7C:
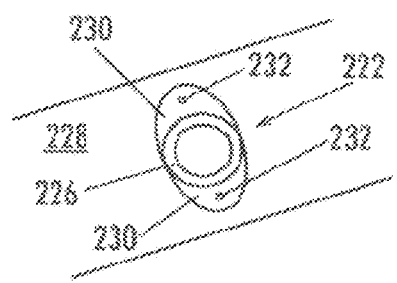
FIG. 7C is a front view of a seroma evacuation tube for anchoring to the skin surface.

The embodiments of FIGS. 6 and 7 are also applicable for use in anchoring a seroma evacuation tube assembly 222, as shown in FIG. 7C. Typically, such a tube is placed at the end of a procedure, such as an endoscopic procedure, within the wound to allow any pockets of fluid that may form to drain. The tube assembly 222 has a first end (not shown) which is positioned within the incision, or existing pocket of fluid. It should be noted that the located of the first end is extremely important. If the first end is placed too shallow, it will not make sufficient contact with the fluid pocket and be able to effectively drain it. If the first end is placed too deeply, it will surpass the fluid pocket and make contact with the surrounding tissue and will not be effective in draining the seroma. Tube assembly also has a second end 226 that is opposed to the first end and is located at the surface of the skin 228. A pair of opposing tabs 230 extend from the second end 226 in opposed directions to form a platform to secure the tube assembly 222. Once secure, the tabs 230 help to maintain a fixed position for the tube assembly 222. Each tab 230 has an anchoring hole 232. Each anchoring hole is used to secure the tube assembly 222 to the skin surface 228. This is done by placing a few sutures or stitches in the skin surface 228 to effectively secure the position of the tube assembly relative to the skin surface. With the present invention, the securing of the tube assembly 222 to the skin surface can be accomplished quickly and easily. The user inserts either a suture length 42 (as shown in FIG. 6) or a second alternative loop suture (as shown in FIG. 7) into the anchoring hole 232 using the suture insertion device 26. Once a portion of the length or loop is embedded into the tissue, the suture insertion device 26 is retrieved leaving a length of self-retaining suture within the tissue. Once the suture is fixed to the tube assembly 222, it effectively anchors the tube assembly in place. This procedure is an improvement over the prior art in that the anchoring method may be accomplished by someone other than a doctor, such as a nurse or medical technician. Furthermore, because the anchoring method of the present invention does not require any movement of the tube assembly 222 during suturing, it is an appropriate application for this procedure. The absence of having to tie off the suture or move the needle in and out during suturing enables the medical professional to quickly and accurately secure the tube assembly 222 into place with minimum pain to the patient and little or no movement of the tube assembly during the process.

Figure 8:
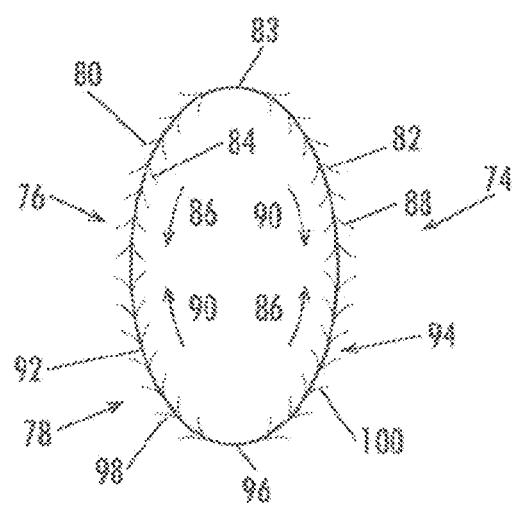
FIG. 8 is a front view of the fourth alternative embodiment of the present invention.

FIG. 8 shows a further alternative embodiment of the present invention. FIG. 8 shows a first alternative looped suture 74 having a first alternative loop half 76 and a second alternative loop half 78. The first alternative loop half 76 includes a first alternative section 80, a second alternative section 82 an intermediate section 83 in between the first 80 and second 82 alternative sections. The first alternative section 80 has first alternative retainers 84 extending from the suture 74 in a first direction shown by arrow 86. The second alternative section 82 has second alternative section retainers 88 extending therefrom in a second direction shown by arrow 90. The first 84 and second 88 alternative section retainers both face the intermediate section 83 and thus each other.

The second alternative loop half 78 is similarly structured to the first alternative loop half 76. The second half 78 includes a third section 92, a fourth section 94 and a second intermediate section 96. The second intermediate section 96 is located between the third 92 and fourth 94 sections. The third section 92 has a plurality of third retainers 98 extending from the periphery of the length of the third section in the second direction, indicated by arrow 90. Similarly, the fourth section 94 has a plurality of fourth retainers 100 extending from the periphery of the length of the fourth section in a first direction, indicated by arrow 86. Because the first and second directions are opposed, as discussed above, the third retainers 98 and the fourth retainers 100 face the second intermediate section 96 and thus each other. The spaces between the first alternative loop half 76 and the second alternative loop half 78 is first alternative empty loop space 102 and has no retainers thereon.

Figure 9:
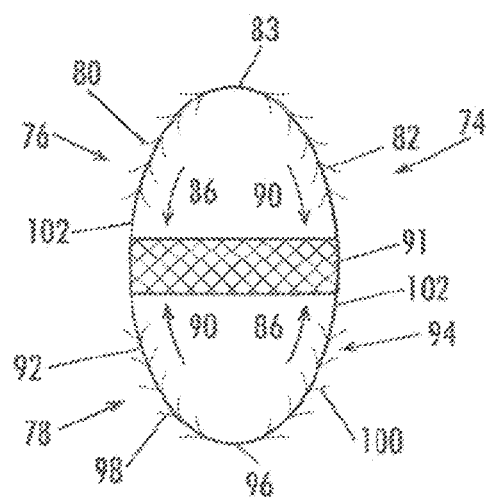
FIG. 9 is a front view of the embodiment of FIG. 8 with a mesh sling attached thereto.

The embodiment of FIG. 8 is shown in FIG. 9 with a mesh sling 91 attached thereto. This enables the assembly of FIG. 11 to support an object such as a bladder neck without cutting into the tissue and also effectively distributing the support load across the sling.

In use as a support for an object, such as the suspension of a bladder neck, the suture insertion device 26 receives a portion of the first intermediate section 83 within its recess 34. The first alternative empty loop space 102 and the mesh sling 91 attached thereto between the first alternative loop half 76 and the second alternative loop half is located under a body part 72 to be supported, such as the bladder neck, as shown diagrammatically in FIG. 11. It should be noted that the sling 91 may be looped over the empty loop space or it may be fixed thereto. The user places the intermediate section 83 within the recess 34 of the suture insertion device 26. The suture insertion device 26 is then inserted into a section of the body of the mammal, typically within a section of tissue that will provide support for the first alternative looped suture 74 upon removal of the suture insertion device, such as a section of muscle. As the suture insertion device 26 moves in a forwardly direction, the finger 36 helps to hold the first alternative looped suture within the recess 34 during forward travel of the suture insertion device. The sharpened underside 38 of the suture insertion device 26 cuts through the mammalian tissue to form an insertion pathway. In addition, as the first alternative looped suture 74 moves in a forwardly direction, the first alternative retainers 84 and second alternative retainers 88 retainers flex and remain close to the perimeter of the first alternative looped suture. When the first alternative retainers 84 and the second alternative retainers 88 of the first alternative looped suture 74 have been completely inserted into the section of tissue, the user stops the forward travel of the suture insertion device 26. The user then begins to remove the suture insertion device 26 by moving the suture insertion device in a direction opposed to the insertion pathway. As this occurs, the opposed movement of the suture insertion device 26 enables the first alternative looped suture 74 to free itself from its location within the recess 34. The finger 36 no longer is able to hold the intermediate section 83 within the recess 34 when the suture insertion device 26 travels in an opposite direction from the insertion pathway. As a result, the intermediate section 83 is freed from its position within the recess 34, and the suture insertion device 26 may be completely removed from the tissue of the mammal by reversing the direction taken on the insertion pathway. At this time any movement of the first alternative loop half 76 in a direction opposed to the insertion pathway would result in the first alternative retainers 84 and the second alternative retainers 88 becoming rigid and opposing movement in a direction opposed to the insertion pathway. This also results in the first alternative retainers 84 and second alternative retainers 88 extending outwardly relative to the periphery of the first alternative looped suture 74 and into the surrounding body of the mammal to secure the position of the suture at that location.

Figure 11:
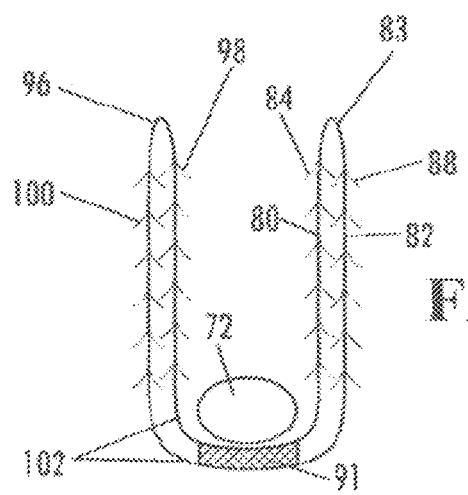
FIG. 11 is a diagrammatic view of the embodiment of FIG. 9 in a proposed installed position for use as a support for a human organ.

Once the suture insertion device 26 is removed from the body of the mammal, the suture insertion device is then used to insert the second alternative loop half 78 of the first alternative looped suture 74 within the body of the mammal. As discussed above, the position of the first alternative empty loop space 102 and mesh sling 91, between the first alternative loop half 76 and the second alternative loop half 78, are checked to ensure that they remain located under the bladder neck to provide support. Thus, with the first alternative loop half 76 already inserted, the user, typically a surgeon or other medical professional, would insert the second alternative loop half 78 into an alternative section of tissue that would be able to provide effective support to the organ. This is accomplished by inserting both halves of the first alternative looped suture 74 at particular locations and angles within the mammalian issue, such that when both halves of the first alternative looped suture 74 are completely inserted, would support and hold the organ in a position or location as medically or surgically desired. FIG. 11 provides a diagrammatic depiction of such an arrangement where the body part 72 is supported by the two halves of the first alternative looped suture 74.

The insertion of the second alternative loop half 78 of the first alternative looped suture 74 is similar in many respects to the steps taken to insert the first alternative loop half 76. To insert the second alternative loop half 78, the user places the second intermediate section 96 within the suture insertion device recess 34 and inserts the suture insertion device 26 into the body of a mammal at the appropriate location and angle relative to the insertion pathway taken with the first alternative loop half 76 to ensure that the subject body part will be supported when the second alternative loop half 78 is fully inserted. Similarly, as discussed above, the user inserts the suture insertion device 26 into a section of the body of the mammal, typically within a section of tissue, such as a section of muscle. As the suture insertion device 26 moves in a forwardly direction, the suture insertion device holds the second alternative looped half 78 within its recess 34 at the second intermediate section 96. The finger 36 helps to hold the second intermediate section 96 within the recess 34 during forward travel of the suture insertion device 26. The sharpened underside 38 of the suture insertion device 26 cuts through the mammalian tissue to form a second insertion pathway. During insertion, the third 98 and fourth 100 retainers flex inwardly toward the periphery of the first alternative looped suture 74 so as to ease forward movement of the suture insertion device 26. When the second alternative loop half 78 has been completely inserted into the selected section of muscle, the user stops the forward travel of the suture insertion device 26. The user then begins to remove the suture insertion device 26 by moving it in a direction opposed to the second insertion pathway. As this occurs, the opposed movement of the suture insertion device 26 enables the second intermediate section 96 to free itself from its location within the recess 34. The finger 36 is no longer able to hold onto the second intermediate section 96 within the recess 34 when the suture insertion device 26 travels in an opposite direction from the second insertion pathway. As a result, the second alternative loop half 78 is freed from its position within the recess 34, and the suture insertion device 26 may be completely removed from the tissue of the mammal by reversing the direction taken on the second insertion pathway. This also results in the third 98 and fourth 100 retainers extending outwardly relative to the periphery of the first alternative looped suture 74 and into the surrounding body of the mammal to secure the position of the second alternative loop half 78 at that location.

Once the first alternative loop half 76 and second alternative loop half 78 of the first alternative looped suture 74 have been inserted into the body of a mammal, the first alternative empty loop space 102 between the first 76 and second 78 halves should be taught and properly positioned under the body part 72 to be supported, as shown in FIG. 11. Any reverse movement of the suture length 10 along the first alternative loop half 76 would result in the first alternative 84 and second alternative 88 retainers becoming rigid and opposing movement in a direction opposed to the first insertion pathway. This enables the first alternative loop half 76 to continue to support the body part 72. Similarly, any reverse movement of the second alternative loop half 78 would result in the third 98 and fourth 100 retainers becoming rigid and opposing movement in a direction opposed to the second insertion pathway. This enables the second alternative loop half 78 to continue to support the body part at the intended location.

Figure 10:
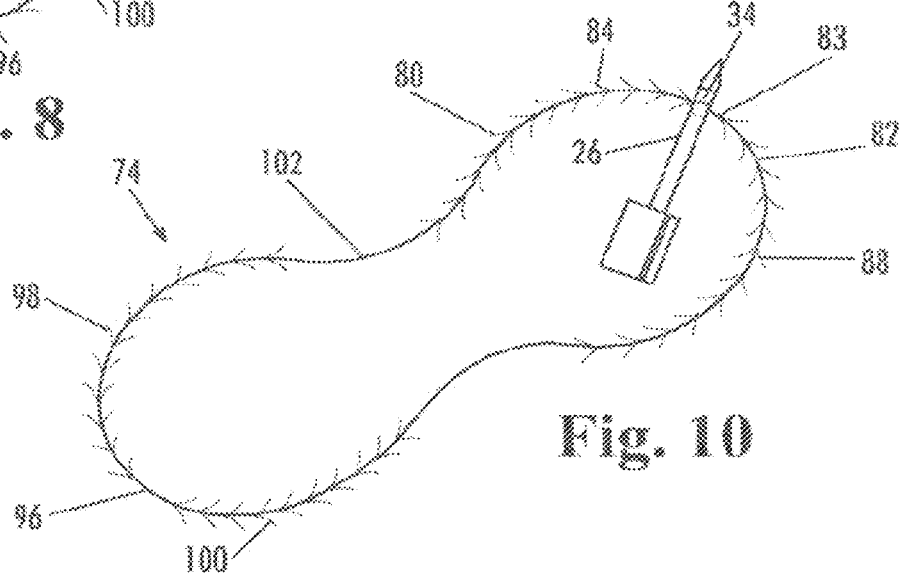
FIG. 10 is a perspective view of the assembly of the embodiment of FIG. 8 and the suture insertion device of FIGS. 2A and 2B.
Figure 12:
FIG. 12 is a front view of an alternative embodiment of FIG. 10 in use for closing an incision where one end of the embodiment of FIG. 10 is inserted using a detachable suture insertion device as shown and the other has an attached curved suture insertion device.
Figure 12:
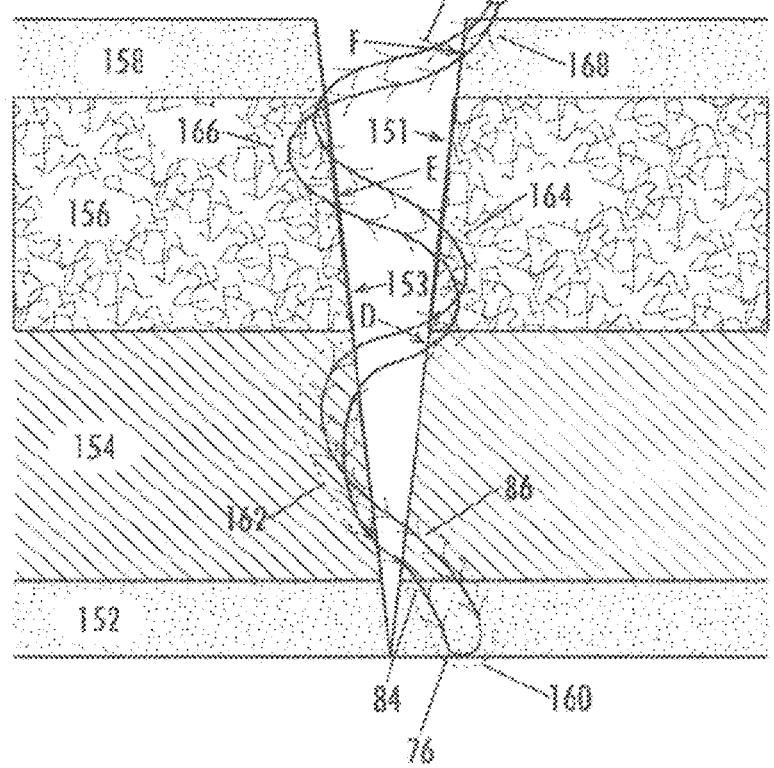

A further alternative use for the embodiment of FIG. 8 is shown in FIGS. 10 and 12. FIG. 10 shows the embodiment of FIG. 9 in assembly with the suture insertion device 26. FIG. 12 shows the use of the looped suture 74 used in the closure of an incision 150 made following an endoscopic procedure. During such a procedure, a relatively small incision is made at the surface of the body. However, the incision, as can be seen in the figure, may be relatively deep to provide access to the desired surgical objective. Upon completion of the procedure the incision 150 made must be effectively closed throughout its full depth in order to prevent the formation of fluid pockets called seromas that can harbor infection. A deep incision requires suturing at a number of levels of different tissue. Further, it is often times difficult to properly close the deepest levels of tissue using present equipment and techniques because of insufficient space to manipulate suture needles. As a result, the present invention provides a significant advancement in this area.

In closing an endoscopic port closure, the user may use the loop suture 74 shown in FIG. 12 and ensure that a portion of the first intermediate section 83 was received within the recess 34 of the suture insertion device 26. In the case of a port closure, the layers of tissue needing closure may include fascia 152, muscle 154, fat 156, and skin 158. The incision 150 creates a pair of opposing incision walls, 151, 153.

As can been seen in FIG. 12, the deepest portion of the incision is narrow. As a result, it is more challenging for a surgeon to effectively manipulate the tissue in this area to properly close the incision. In view of this challenge, it is most effective to use a curved, detached suture insertion device in this application rather than a straight suture insertion device or an attached suture insertion device that would require detachment and tying off. It should be noted that where there is more space or a different location where the tissue is more accessible, a straight suture insertion device or an attached suture insertion device may be more effective. The curved suture insertion device 27, as shown in FIG. 12A offers the advantage of being able to create curved insertion pathways that can easily weave between two sides of an incision, as shown in FIG. 12 to effectively close all layers of tissue in the incision.

Figure 12A:
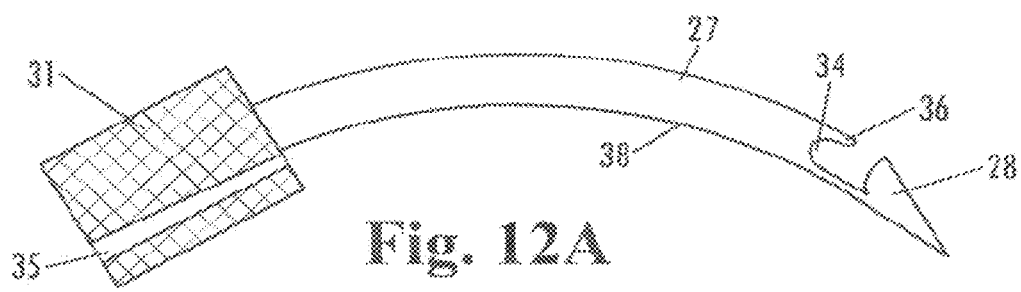
FIG. 12A is a front view of an alternative suture insertion device

The curved suture insertion device 27, as shown in FIG. 12A, is the same in all respects to the suture insertion device 26 shown in FIGS. 2A, 2B and 4 except that the curved device has a radius of curvature along the suture insertion device body 25A rather than a straight length. Thus, reference to the suture insertion device recess 34 and the other features of the suture insertion device will be the same for both configurations where applicable. It should also be noted that the radius of curvature of the suture insertion device body 25A, like the length and diameter, are determined by the application and suture size used.

Figure 12B:
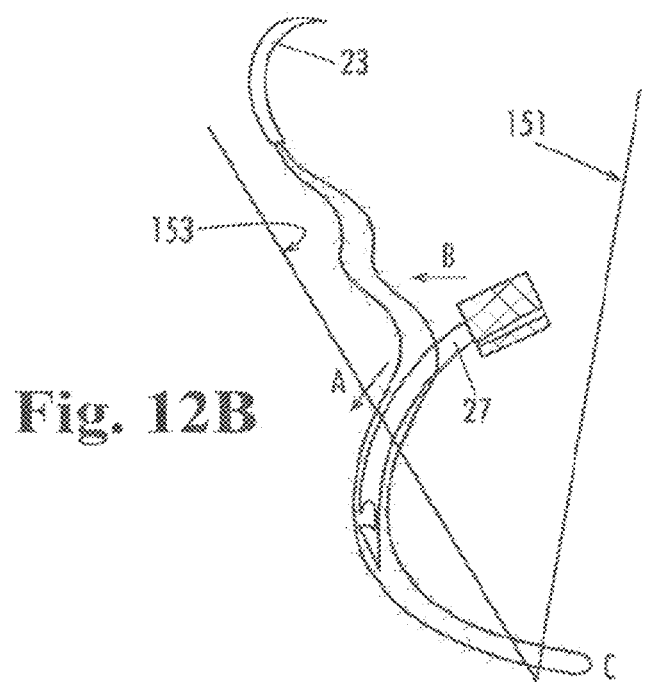
FIG. 12B is a front view of the embodiment of FIG. 12 showing the insertion and removal of the curved suture insertion device, as shown in FIG. 12A.

To initiate the closing of the port closure of FIG. 12, the curved suture insertion device 27 is inserted into the deeper tissues, such as the muscle 152 at point A. The curved suture insertion device is pushed into the incision wall 153 at point A until at least a portion of the curved suture insertion device body 25A and the first alternative loop half 76 held within the recess 34 are embedded in the muscle 154 tissue. At that point, the curved suture insertion device 27 is pivoted toward the incision as indicated by arrow B so that a portion of the first end 28 of the device 27 and the loop half exit the incision wall 153 and reenter incision wall 151. As the user continues to pivot the curved suture insertion device 27, a portion of the curved suture insertion device body 25A that holds the first alternative loop half 76 is urged forwardly and becomes embedded in the fascia tissue 152. As discussed above, the finger 36 helps to hold the first alternative loop half 76 within the recess 34 during forward travel of the curved suture insertion device 27. Also as discussed above, as the first alternative loop half 76 moves in a forwardly direction, the first alternative retainers 84 and second alternative retainers 88 retainers flex and remain close to the perimeter of the first alternative loop half 76. Moreover, as the curved suture insertion device is inserted into the incision wall 153 and rotated therein, it creates a curved insertion pathway 160. Once the surgeon has effectively embedded at least a portion of the first alternative loop half 76 in the fascia tissue 152, forward movement of the curved insertion device and the first alternative loop half 76 stop at point C in FIG. 12B.

To retrieve the curved suture insertion device 27, the user reverses the travel along the curved insertion pathway 160. As this occurs, the opposed movement of the curved suture insertion device 27 enables the first alternative loop half 76 to free itself from its location within the recess 34. The finger 36 no longer is able to hold the intermediate section 83 within the recess 34. As a result, the intermediate section 83 is freed from its position within the recess 34, and the curved suture insertion device 27 may be completely retrieved from the incision wall 153 at the point of entry A. To secure the first loop half 76 within the incision and effectively bind the incision walls 151, 153 together, the user would pull on the embedded first alternative loop half 76 at the first alternative empty loop space 102 to create tension in the loop half and pull the incision walls 151, 153 together. At this time any movement of the first alternative loop half 76 in a direction opposed to the curved insertion pathway 160 would result in the first alternative retainers 84 and the second alternative retainers 88 becoming rigid and opposing movement in a direction opposed to the insertion pathway. This also results in the first alternative retainers 84 and second alternative retainers 88 extending outwardly relative to the periphery of the first alternative looped half 76 and into the surrounding body of the tissue to secure the position of the first alternative loop half 76 at that location.

Once the curved suture insertion device 27 is removed, an attached, curved needle 23 is then used to insert the second alternative loop half 78 of the first alternative looped suture 74 to close the remaining layers of tissue. An attached curved needle 23 is appropriate in this application because the suture pathway for closing the second half of the incision is upward, out of the incision where the surgeon will have adequate space to tie off the suture ends. The attached curved needle 23 is fixedly attached to the second intermediate section 96 of the second alternative loop half 78. It should be noted that the curved suture insertion device 23 may also be fixedly attached to two free ends of a length of self-retaining suture rather than a loop end. The function of the fixed suture insertion device and self-retaining suture attached thereto remains the same.

The insertion of the second alternative loop half 78 is similar in many respects to the steps taken to insert the first alternative loop half 76. The user inserts the curved needle 23 with the second alternative loop half 78 fixed thereto into the tissue on the opposed side of the incision from the exit point of the first alternative loop half 76 at point D in FIG. 12. Similarly with the first insertion of the curved suture insertion device 27, the curved suture insertion device 23 is inserted into the incision wall 151 and moved inwardly. Then the curved suture insertion device 23 is pivoted so that the first end 28 of the suture insertion device exits the incision wall 151 and reenters the opposing incision wall 153 at point E. The curved suture insertion device 23 is inserted as discussed above into the incision wall 153 and then pivoted so as to cause the first end 28 to exit the incision wall 153 and reenter the opposing wall 151 at point F. Once the curved suture insertion device 23 exits the skin 158, the user pulls on the second alternative loop half 78 so that it is in tension Once the second alternative loop half 78 is pulled taught, the lengths extending outside the skin may be cut back to reduce accidental pulling or catching. It should be noted that the second portion of the above closing procedure may be accomplished with a detached suture insertion device using the suture of the present invention. Alternatively, a straight suture insertion device, attached or detached, may be used in the appropriate circumstance. The use of curved and straight, and attached and detached suture insertion devices will vary depending upon the particular procedural situation as discussed above.

Figure 13:
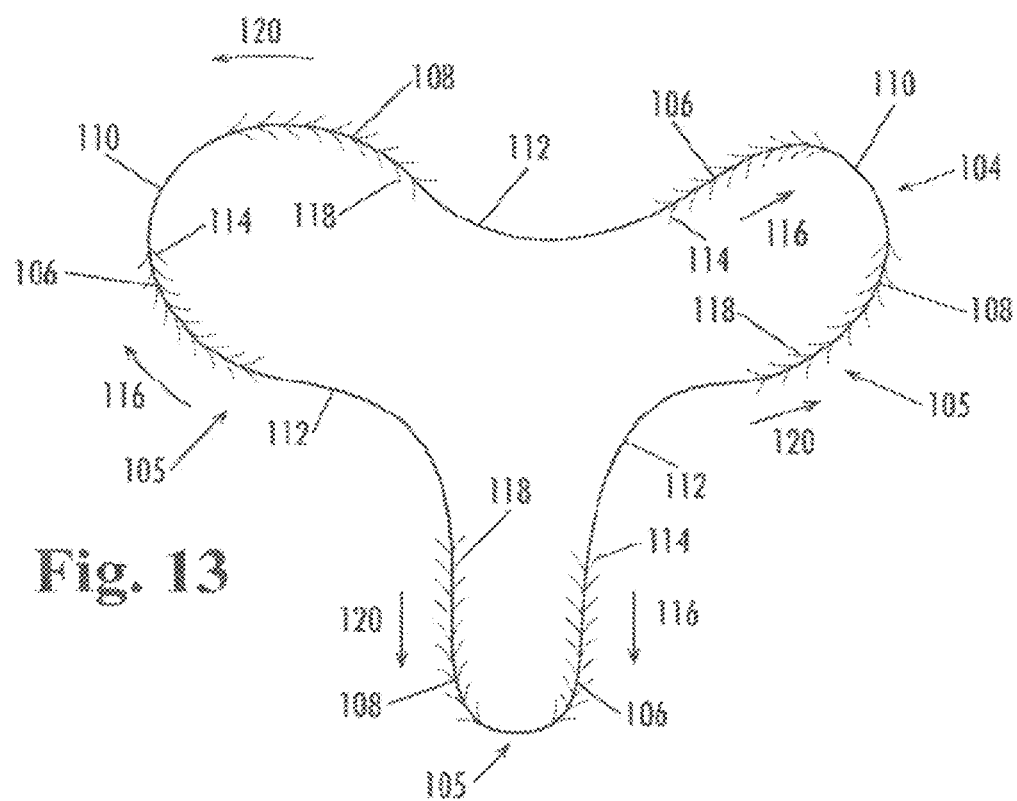
FIG. 13 is a front view of the fifth alternative embodiment of the present invention.

The above provide examples of several different types of suture configurations that may be used for support of body parts, to bind wounds or close incisions created during surgical procedures. FIG. 13 shows a further alternative loop configuration that has multiple loop sections. A multi-sectional looped suture may be used in a number of different surgical or medical procedures, including the support of an organ, such as the bladder neck discussed above it is anticipated that the multi-sectional looped suture may also have other applications such as the support or binding of other body parts, or the binding or closing of wounds or incisions that require a multi-point approach in the repair or procedure. For example, in a wound that has multiple tears or rips, a multi-sectional loop may be an appropriate suture for repair in that it may be able to pull all sections of the wound together without having to resort to the use of multiple lengths of suture. In addition, one advantage of using a multi-sectional looped suture is that the self-retaining sutures are inserted into the tissue below the skin line and thus pull the tissue or sections of the wound together so that there may not need to be any sutures on the skin surface. This results in the ability to allow the wound to heal without additional sutures on the skin surface which may minimize the chance of further scarring.

FIG. 13 shows a length of suture where the ends are joined to form a multi-sectional loop 104. The multi-sectional loop 104 has three sections 105. Each section 105 has a first length 106, a second length 108, and an intermediate length 110. The first length 106 has first length retainers 114 extending peripherally from the first length in a first direction shown by arrow 116. The second length 108 has second length retainers 118 extending peripherally from the second length in a second direction shown by arrow 120 which is opposed to the first direction. The first length retainers 114 along the first length 106 and the second length retainers 118 along the second length 108 face the intermediate length 110 and each other. The empty loop space 112 is that length of the multi-sectional loop 104 that is not an intermediate length 110 that has no retainers thereon. The empty loop space 112 on the multi-sectional loop 104 also separates each section 105.

In use, the multi-sectional loop 104 may be used to support a body part, or to close a multi-angled wound or incision. To close a wound, one intermediate length 110 of one of the sections 105 of the multi-sectional loop 104 is inserted into recess 34 of the suture insertion device 26. The suture insertion device 26 is then inserted into the side of a section of tissue that is the subject of the wound or incision to be closed. With the intermediate length 110 of one of the sections 105 of the multi-sectional loop 104 held within the recess 34 of the suture insertion device 26, the suture insertion device is moved in a forwardly direction. As the suture insertion device 26 moves, it holds a portion of the intermediate length 110 within its recess 34. The sharpened underside 38 of the suture insertion device 26 cuts through the mammalian tissue to form a first insertion pathway indicated by the dashed line 122. As the section 105 moves in a forwardly direction, the first length 114 and second length 118 retainers flex and remain close to the perimeter of the length of the multi-sectional loop 104. When the first length 114 and second length 118 retainers are completely embedded within the tissue, the user stops the forward travel of the suture insertion device 26. The user then begins to remove the suture insertion device 26 by moving it in a direction opposed to the first insertion pathway 122. As this occurs, the opposed movement of the suture insertion device 26 enables the intermediate length 110 to free itself from its location within the recess 34. The finger 36 no longer is able to hold the intermediate length 110 within the recess 34 when the suture insertion device 26 travels in an opposite direction from the insertion pathway 122. As a result, the inserted section of the multi-sectional loop 104 is freed from its position within the recess 34, and the suture insertion device 26 may be completely removed from the tissue of the mammal by reversing the direction taken on the insertion pathway. At this time any movement of the inserted section in a direction opposed to the first insertion pathway 122 would result in the first length retainers 114 and second length retainers 118 becoming rigid and would oppose movement in a direction opposite to the first insertion pathway 122. This also results in the first length retainers 114 and second length retainers 118 extending outwardly relative to the periphery of the inserted section 105 of the multi-sectional loop 104 and into the surrounding tissue to secure the position of the inserted section 105 and the section of tissue held by that inserted section.

Figure 14A:
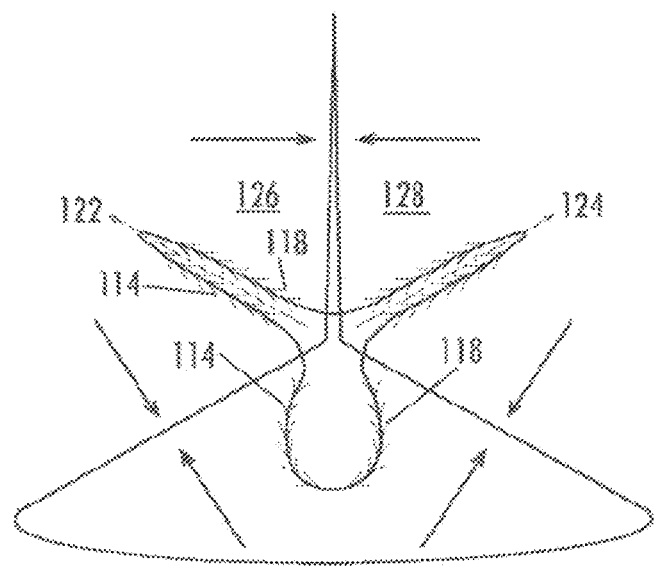
FIG. 14A is a diagrammatic view of the embodiment of FIG. 13 as it is being installed.
Figure 14B:
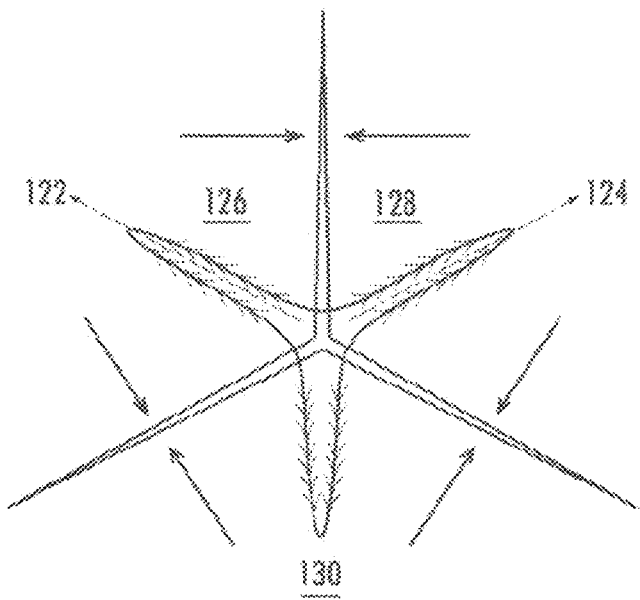
FIG. 14B is a diagrammatic view of the embodiment of FIG. 13 in its fully installed position.

The process of wound or incision closure is repeated as described above with the insertion of the suture insertion device 26 into a second section of tissue to create a second insertion pathway 124 to bind the first 126 and second 128 sections of tissue together, as shown in FIG. 14A. The process is repeated yet again where the user inserts the suture insertion device into the third section of tissue 130 to create a third insertion pathway 132 and to bind the third section of tissue with the first 126 and second 128 sections of tissue. FIG. 14B shows the multi-sectional loop 104 in its frilly installed position.

It is appreciated that the multi-sectional loop 104 described above may include additional loop sections and may be used to bind wounds that have multiple sections, not presently shown in FIGS. 14A and 14B. It is further appreciated that the multi-sectional loop 104 described above or other multi-sectional loops having additional converging loop portions may be used on surgical or medical procedures, such as the bladder support procedure described above. It is appreciated that the multi-sectional loop configurations provides additional support points (more than two such a procedure. Additional support points may result in more effective support and thus a greater chance of success of the procedure.

Figure 15:
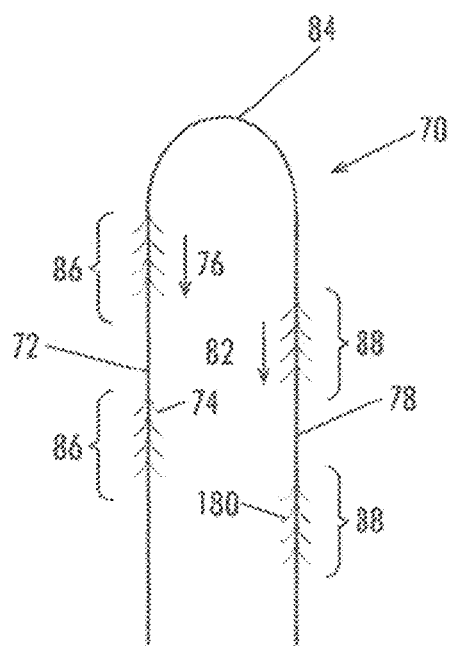
FIG. 15 is a front view of an alternative placement of the self-retaining suture of the present invention.

FIG. 15 shows a further alternative embodiment 170 of the present invention. A first free length of suture 172 is shown having first alternating retainers 174 extending peripherally from the length at alternating intervals in a first direction shown by arrow 176. The embodiment also has a second free length of suture 178 having second alternating retainers 180 extending peripherally from the length at alternating intervals in a second direction shown by arrow 182. The first 172 and second 178 free lengths of suture are separated by a midsection 184. The first alternating retainers 174 are located along the length of the free length of suture 172 at first intervals 186 and the second alternating retainers 180 are located along the length at second intervals 188 so that when the free length of suture 170 is inserted into the tissue of a mammal, and the first 172 and second 178 free lengths are placed relatively adjacent to one another, there is no overlap of first intervals 186 with the second intervals 188, and thus the first alternating retainers 174 do not overlap the second alternating retainers 180 as shown in FIG. 15.

Figure 16:
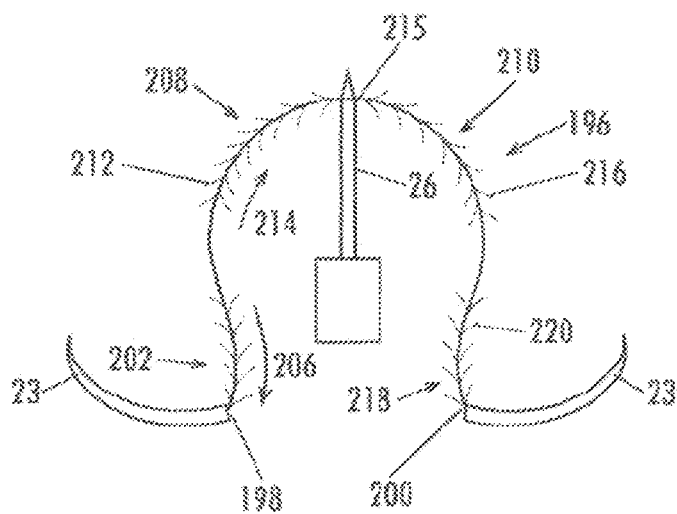
FIG. 16 is a front view of a sixth alternative embodiment of the present Invention with the suture insertion device of FIGS. 2A and 2B.

FIG. 16 shows a further alternative embodiment of the present invention. FIG. 16 shows a multi-sectional length of suture 196 having free ends 198, 200. The suture 196 has four sections of retainers thereon. The first section 202 has first section retainers 204 extending outwardly in a first direction shown by arrow 206. The second 208 and third 210 sections have converging retainers thereon. The second section 208 has second section retainers 212 facing a second direction shown by arrow 214 and the third section 210 has third section retainers 216 facing in the first direction. The first and second directions are opposed and thus the second 212 and third 216 section retainers face each other at converging point 215. The third section retainers 216 are also in the same direction as the first section retainers 204. The fourth section 218 has fourth section retainers 220 that face in the second direction and face away from the third section retainers 216 but face in the same direction as the second section retainers 212.

In use, this embodiment would likely be used to anchor or support an object or organ, or for closing an endoscopic access port. The second 208 and third 210 sections would first be anchored into tissue using the suture insertion device 26 described above. The suture insertion device 26 is shown in FIG. 16 using a straight length 32, however, it is anticipated that a curved suture insertion device 27 may also be used when appropriate. Subsequently, the first section 202 would be anchored into neighboring tissue using a curved needle 23, (as shown) or straight needle, that is either attached (as shown) or detachable from the suture using the suture insertion device of the present invention. Similarly, the fourth section 218 would be anchored in the same fashion in neighboring tissue by inserting either a straight or curved detachable suture insertion device as described above, or by an attached conventional needle or curved needle 23 as shown. This embodiment provides for the flexibility in surgical applications where the anchoring of some section of self-retaining suture is needed where access to the area is limited while other sections may have more accessibility and an attached needle may be more appropriate.

It is anticipated that the detachable suture insertion device may be automated to some degree. It is anticipated that the suture insertion device may include a mechanism for moving the needle body from a first, initial position to a second installed position within the body. It is anticipated that the mechanism would be moveably linked to the needle body so that during installation, the mechanism would be able to move the needle body, and thus the recess and suture therein, from a first position to a second installed position within the body upon activation. It is further anticipate that the mechanism may be spring loaded. Such a mechanism would provide a further level of accuracy and efficacy in placing a self-retaining suture in a desired location, especially in situations that are currently present challenges in that regard. A spring loaded device would provide further accuracy because the length of extension and retraction of the needle body could be predetermined with great accuracy. Use of an automated mechanism would enable a surgeon to place the suture and any attachment in a specific location without having to reach that location and with greater confidence in the accuracy of the placement. Incorporation of the present invention would further increase overall efficacy of the procedure and minimize pain and possible infection to the patient. These effects would decrease the overall recovery time and decrease the overall cost of the procedure.

Because it is anticipated that the present invention may be automated to some degree, it is anticipated that the present invention may be used in an automated surgical system. Due to the high level of accurate placement of the suture and any attachment, the present invention is an ideal candidate to be used with a robotic surgical system or minimally invasive surgical procedures.

While the invention has been described in detail with respect to specific preferred embodiments thereof, numerous modifications to these specific embodiments will occur to those skilled in the art upon a reading and understanding of the foregoing description; such modifications are embraced within the scope of the present invention.

What is claimed is:

1. A self-retaining suture comprising:
   (a) a first body section comprising:
      (i) a first portion that includes a first plurality of retainers projecting peripherally from the first portion along at least a portion thereof in a first direction,
      (ii) a second portion that includes a second plurality of retainers projecting peripherally from the second portion along at least a portion thereof in a second direction opposite to the first direction, and
      (iii) a first intermediate portion disposed between the first and second portions, where the first and second pluralities of retainers face the first intermediate portion; and
   (b) a second body section coupled with the first body section, wherein the second body section comprises:
      (i) a third portion that includes a third plurality of retainers projecting peripherally from the third portion along at least a portion thereof in the second direction,
      (ii) a fourth portion that includes a fourth plurality of retainers projecting peripherally from the fourth portion along at least a portion thereof in the first direction, and
      (iii) a second intermediate portion disposed between the third and fourth portions, wherein the third and fourth pluralities of retainers face the second intermediate portion.

2. The self-retaining suture of claim 1, wherein the self-retaining suture forms a complete 360-degree loop.

3. The self-retaining suture of claim 1, further comprising first and second terminal ends that are joined together to make the self-retaining suture into a complete 360-degree loop.

4. The self-retaining suture of claim 1, wherein at least one of the first or second pluralities of retainers projects on first and second opposing lateral sides of the first portion of the first body section.

5. The self-retaining suture of claim 1, wherein each of the first and second pluralities of retainers projects on first and second opposing lateral sides of the first portion of the first body section.

6. The self-retaining suture of claim 1, wherein at least one of the first, second, third, or fourth pluralities of retainers is configured to generally flex toward the respective first, second, third, and fourth portions when the self-retaining suture is inserted into tissue to minimize damage to the tissue by the first, second, third, or fourth pluralities of retainers.

7. The self-retaining suture of claim 1, wherein the first plurality of retainers are disposed adjacent to the third plurality of retainers.

8. The self-retaining suture of claim 1, wherein the second plurality of retainers are disposed adjacent to the fourth plurality of retainers.

9. The self-retaining suture of claim 1, wherein the first, second, third, and fourth pluralities of retainers are configured to generally flex toward the respective first, second, third, and fourth portions when the self-retaining suture is inserted into tissue to minimize damage to the tissue by the first, second, third, and fourth pluralities of retainers during insertion.

10. The self-retaining suture of claim 9, wherein the first, second, third, and fourth pluralities of retainers are configured to generally resist movement through the tissue when the suture is pulled in a direction opposite to the direction of insertion.

11. The self-retaining suture of claim 1, wherein the first body section includes a first empty portion having no retainers disposed thereon, wherein the second body section includes a second empty portion having no retainers disposed thereon, wherein the first empty portion separates the first plurality of retainers from the third plurality of retainers, wherein the second empty portion separates the second plurality of retainers from the fourth plurality of retainers.

12. The self-retaining suture of claim 1, wherein the first body section is a first loop half, wherein the second body section is a second loop half, wherein the first and second loop halves form a complete 360-degree loop.

13. The self-retaining suture of claim 1, further comprising a third body section coupled with the first and second body sections, wherein the third body section comprises:
(i) a fifth portion that includes a fifth plurality of retainers projecting peripherally from the fifth portion along at least a portion thereof in the first direction,
(ii) a sixth portion that includes a sixth plurality of retainers projecting peripherally from the sixth portion along at least a portion thereof in the second direction, and
(iii) a third intermediate portion disposed between the third and fourth portions, wherein the fifth and sixth pluralities of retainers face the third intermediate portion.

14. The self-retaining suture of claim 13, wherein the first body section includes a first empty portion having no retainers disposed thereon, wherein the second body section includes a second empty portion having no retainers disposed thereon, wherein the third body section includes a third empty portion having no retainers disposed thereon.

15. The self-retaining suture of claim 14, wherein the first plurality of retainers are separated from the sixth plurality of retainers by the first empty portion, wherein the second plurality of retainers are separated from the fourth plurality of retainers by the second empty portion, wherein the third plurality of retainers are separated from the fifth plurality of retainers by the third empty portion.

16. A continuous loop of self-retaining suture comprising:
(a) a first body section comprising:
(i) a first portion that includes a first plurality of retainers projecting peripherally from the first portion along at least a portion thereof in a first direction, wherein the first plurality of retainers are configured to generally flex toward the first portion when the self-retaining suture is inserted into tissue,
(ii) a second portion that includes a second plurality of retainers projecting peripherally from the second portion along at least a portion thereof in a second direction opposite to the first direction, wherein the second plurality of retainers are configured to generally flex toward the second portion when the self-retaining suture is inserted into the tissue, and
(iii) a first intermediate portion disposed between the first and second portions, where the first and second pluralities of retainers face the first intermediate portion; and
(b) a second body section coupled with the first body section, wherein the second body section comprises:
(i) a third portion that includes a third plurality of retainers projecting peripherally from the third portion along at least a portion thereof in the second direction,
(ii) a fourth portion that includes a fourth plurality of retainers projecting peripherally from the fourth portion along at least a portion thereof in the first direction, and
(iii) a second intermediate portion disposed between the third and fourth portions, wherein the third and fourth pluralities of retainers face the second intermediate portion.

17. The continuous loop of self-retaining suture of claim 16, wherein the first body section is a first loop half, wherein the second body section is a second loop half, wherein the first and second loop halves form a complete 360-degree enclosed loop.

18. The continuous loop of self-retaining suture of claim 16, wherein the first body section includes a first empty portion having no retainers disposed thereon, wherein the second body section includes a second empty portion having no retainers disposed thereon, wherein the first plurality of retainers are separated from the third plurality of retainers by the first empty portion, wherein the second plurality of retainers are separated from the fourth plurality of retainers by the second empty portion.

19. The continuous loop of self-retaining suture of claim 16, further comprising a third body section coupled with the first and second body sections, wherein the third body section comprises:
(i) a fifth portion that includes a fifth plurality of retainers projecting peripherally from the fifth portion along at least a portion thereof in the first direction,
(ii) a sixth portion that includes a sixth plurality of retainers projecting peripherally from the sixth portion along at least a portion thereof in the second direction, and
(iii) a third intermediate portion disposed between the third and fourth portions, wherein the fifth and sixth pluralities of retainers face the third intermediate portion.

20. A system comprising:
(a) a suture insertion device; and
(b) a continuous loop of self-retaining suture comprising:
(i) a first body section comprising:
(A) a first portion that includes a first plurality of retainers projecting peripherally from the first portion in a first direction, wherein the first plurality of retainers projects on first and second lateral sides of the first portion,
(B) a second portion that includes a second plurality of retainers projecting peripherally from the second portion in a second direction opposite to the first direction, and
(C) a first intermediate portion disposed between the first and second portions, where the first and second pluralities of retainers face the first intermediate portion, wherein the first intermediate portion is configured to be received by the suture insertion device, and
(ii) a second body section coupled with the first body section, wherein the second body section comprises:
(A) a third portion that includes a third plurality of retainers projecting peripherally from the third portion along at least a portion thereof, in the second direction,
(B) a fourth portion that includes a fourth plurality of retainers projecting peripherally from the fourth portion in the first direction, and
(C) a second intermediate portion disposed between the third and fourth portions, wherein the third and fourth pluralities of retainers face the second intermediate portion, wherein the second intermediate portion is configured to be received by the suture insertion device.

* * * * *